United States Patent
Tizhoosh et al.

(10) Patent No.: US 11,769,582 B2
(45) Date of Patent: Sep. 26, 2023

(54) SYSTEMS AND METHODS OF MANAGING MEDICAL IMAGES

(71) Applicant: Huron Technologies International Inc., St. Jacobs (CA)

(72) Inventors: Hamid Reza Tizhoosh, St. Jacobs (CA); Wafik Wagdy Moussa, St. Jacobs (CA); Savvas Damaskinos, St. Jacobs (CA); Patrick Myles, St. Jacobs (CA); Alfonso Carlos Ribes, St. Jacobs (CA)

(73) Assignee: HURON TECHNOLOGIES INTERNATIONAL INC., St. Jacobs (CA)

( * ) Notice: Subject to any disclaimer, the term of this patent is extended or adjusted under 35 U.S.C. 154(b) by 513 days.

(21) Appl. No.: 16/674,508

(22) Filed: Nov. 5, 2019

(65) Prior Publication Data
US 2020/0176102 A1 Jun. 4, 2020

Related U.S. Application Data

(60) Provisional application No. 62/755,862, filed on Nov. 5, 2018.

(51) Int. Cl.
*G16H 30/20* (2018.01)
*G06F 16/53* (2019.01)
(Continued)

(52) U.S. Cl.
CPC ............ *G16H 30/20* (2018.01); *G06F 16/53* (2019.01); *G06F 18/2137* (2023.01);
(Continued)

(58) Field of Classification Search
CPC ...... G06F 16/53; G06V 10/40; G06V 10/467; G06K 9/6215; G06K 9/6218; G06K 9/6251
See application file for complete search history.

(56) References Cited

U.S. PATENT DOCUMENTS

| | | |
|---|---|---|
| 4,991,092 A | 2/1991 | Greensite |
| 5,136,660 A | 8/1992 | Flickner et al. |
| | (Continued) | |

FOREIGN PATENT DOCUMENTS

| | | |
|---|---|---|
| EP | 1912160 | 4/2008 |
| WO | 2008089129 | 7/2008 |

OTHER PUBLICATIONS

Hoang, et al., "Invariant pattern recognition using the RFM descriptor," Pattern Recognition, vol. 45, pp. 271-284, 2012.
(Continued)

*Primary Examiner* — Jonathan Ng

(57) ABSTRACT

Computer-implemented methods and systems are provided for managing one or more images. An example method for indexing involves operating a processor to, divide an image portion of an image of the one or more images into a plurality of patches, for each patch of the image: detect one or more features of the patch; and assign the patch to at least one cluster of a plurality of clusters of the image, based on the one or more features of the patch. The processor is operable to, for each cluster of the image, select at least one patch from the cluster as at least one representative patch for the cluster; for each representative patch, generate an encoded representation based on one or more features of the representative patch; and generate an index identifier for the image based on the encoded representations of the representative patches of the image.

22 Claims, 17 Drawing Sheets

(51) Int. Cl.

| | | |
|---|---|---|
| *G06V 10/46* | (2022.01) | |
| *G06F 18/22* | (2023.01) | |
| *G06F 18/23* | (2023.01) | |
| *G06F 18/2137* | (2023.01) | |
| *G06V 10/75* | (2022.01) | |
| *G06V 10/762* | (2022.01) | |
| *G06V 10/764* | (2022.01) | |
| *G06V 10/50* | (2022.01) | |
| *G06V 20/69* | (2022.01) | |
| *G06V 10/82* | (2022.01) | |

(52) U.S. Cl.
CPC .............. *G06F 18/22* (2023.01); *G06F 18/23* (2023.01); *G06V 10/467* (2022.01); *G06V 10/50* (2022.01); *G06V 10/753* (2022.01); *G06V 10/762* (2022.01); *G06V 10/764* (2022.01); *G06V 20/695* (2022.01); *G06V 20/698* (2022.01); *G06V 10/462* (2022.01); *G06V 10/82* (2022.01)

(56) References Cited

U.S. PATENT DOCUMENTS

| | | | |
|---|---|---|---|
| 5,243,655 | A | 9/1993 | Wang |
| 5,270,926 | A | 12/1993 | Tam |
| 5,288,977 | A | 2/1994 | Amendiola et al. |
| 5,463,666 | A | 10/1995 | Eberhard et al. |
| 5,524,068 | A | 6/1996 | Kacandes et al. |
| 5,592,374 | A | 1/1997 | Fellegara et al. |
| 5,969,325 | A | 10/1999 | Hecht et al. |
| 6,424,737 | B1 | 7/2002 | Rising |
| 6,714,665 | B1 | 3/2004 | Hanna et al. |
| 6,798,914 | B1 | 9/2004 | Nanni |
| 7,239,750 | B2 | 7/2007 | Rising |
| 7,949,186 | B2 | 5/2011 | Grauman et al. |
| 8,086,587 | B2 | 12/2011 | Obana et al. |
| 8,117,071 | B1 | 2/2012 | Fitch et al. |
| 8,494,268 | B2 | 7/2013 | Soederberg et al. |
| 8,774,509 | B1* | 7/2014 | Yagnik ................ G06T 9/00 382/218 |
| 8,872,814 | B1 | 10/2014 | Agaian et al. |
| 8,879,120 | B2 | 11/2014 | Thrasher et al. |
| 9,081,822 | B2 | 7/2015 | Xu et al. |
| 9,122,955 | B2 | 9/2015 | Greenspan et al. |
| 9,316,743 | B2 | 4/2016 | Rousso et al. |
| 9,342,893 | B1* | 5/2016 | Wiley ................... G06K 9/6201 |
| 9,361,698 | B1 | 6/2016 | Song et al. |
| 9,495,571 | B1 | 11/2016 | Xiao et al. |
| 9,535,928 | B2 | 1/2017 | Xu et al. |
| 9,710,491 | B2* | 7/2017 | Ke ...................... G06F 16/5838 |
| 9,710,695 | B2 | 7/2017 | Xu et al. |
| 10,176,202 | B1* | 1/2019 | Newman ............ G06F 18/22 |
| 2004/0133927 | A1 | 7/2004 | Sternberg et al. |
| 2004/0240737 | A1 | 12/2004 | Lim et al. |
| 2005/0001033 | A1 | 1/2005 | Cheong et al. |
| 2005/0103856 | A1 | 5/2005 | Zhu |
| 2006/0204042 | A1 | 9/2006 | Hammoud et al. |
| 2006/0257010 | A1 | 11/2006 | George et al. |
| 2007/0181691 | A1 | 8/2007 | Chang |
| 2007/0196007 | A1* | 8/2007 | Chen ................... A61B 6/00 382/131 |
| 2008/0078836 | A1 | 4/2008 | Tomita |
| 2008/0260200 | A1 | 10/2008 | Suzaki |
| 2009/0001167 | A1 | 1/2009 | Usuba |
| 2009/0060303 | A1* | 3/2009 | Douglass ............. G02B 21/244 382/128 |
| 2009/0121027 | A1 | 5/2009 | Nadabar |
| 2009/0322489 | A1 | 12/2009 | Jones et al. |
| 2010/0008589 | A1 | 1/2010 | Bober et al. |
| 2010/0014780 | A1 | 1/2010 | Kalayeh |
| 2010/0046753 | A1 | 2/2010 | Inami et al. |
| 2010/0067799 | A1 | 3/2010 | Liu et al. |
| 2010/0104148 | A1 | 4/2010 | Bovik et al. |
| 2010/0187311 | A1 | 7/2010 | van der Merwe et al. |
| 2010/0188580 | A1* | 7/2010 | Paschalakis ........... G06V 20/40 348/E5.062 |
| 2011/0043864 | A1 | 2/2011 | Tian et al. |
| 2011/0075931 | A1 | 3/2011 | Chiou et al. |
| 2011/0106782 | A1* | 5/2011 | Ke ...................... G06F 16/5838 707/E17.02 |
| 2011/0128566 | A1 | 6/2011 | Eum et al. |
| 2011/0158533 | A1* | 6/2011 | Gutelzon ............ G06F 16/5854 382/176 |
| 2011/0317004 | A1 | 12/2011 | Tao |
| 2012/0043377 | A1 | 2/2012 | Haar et al. |
| 2012/0173347 | A1 | 7/2012 | Neves et al. |
| 2013/0001290 | A1 | 1/2013 | Trajkovic et al. |
| 2013/0022231 | A1 | 1/2013 | Nepomniachtchi et al. |
| 2013/0048731 | A1 | 2/2013 | Flickner et al. |
| 2013/0098983 | A1 | 4/2013 | Neff |
| 2013/0343654 | A1* | 12/2013 | Demoulin ............ G06V 10/462 382/192 |
| 2014/0044361 | A1 | 2/2014 | Lee |
| 2014/0056402 | A1 | 2/2014 | Kikuchi et al. |
| 2014/0142979 | A1 | 5/2014 | Mitsunaga |
| 2014/0241585 | A1 | 8/2014 | Zafiroglu et al. |
| 2014/0263674 | A1 | 9/2014 | Cerveny |
| 2014/0307934 | A1 | 10/2014 | Batenburg et al. |
| 2015/0363660 | A1* | 12/2015 | Vidal ..................... G06V 10/50 382/173 |
| 2016/0203379 | A1 | 7/2016 | Hakim et al. |
| 2016/0239972 | A1* | 8/2016 | Zhu ....................... G06T 7/337 |
| 2017/0091281 | A1 | 3/2017 | Tizhoosh |
| 2017/0091580 | A1* | 3/2017 | Song ....................... G06T 3/40 |
| 2018/0360427 | A1* | 12/2018 | Nakano ..................... G06T 7/74 |
| 2019/0259492 | A1* | 8/2019 | Reicher ................... G16H 30/20 |
| 2019/0303706 | A1 | 10/2019 | Tizhoosh |
| 2020/0163641 | A1* | 5/2020 | Amit ....................... A61B 6/502 |
| 2020/0334486 | A1* | 10/2020 | Joseph ..................... G06T 5/20 |

OTHER PUBLICATIONS

Jadhav, et al., "Feature extraction using radon and wavelet transforms with application to face recognition," Neurocomputing, vol. 72, pp. 1951-1959, 2009.

Zhao, et al., "Retrieval of ocean wavelength and wave direction from sar image based on radon transform," in IEEE International Geoscience and Remote Sensing Symposium, 2013, pp. 1513-1516, Jul. 21-26, 2013, Melbourne, Victoria, Australia.

Chen, et al., "Invariant description and retrieval of planar shapes using radon composite features,"IEEE Transactions on Signal Processing, vol. 56(10), pp. 4762-4771, 2008.

Tabbone, et al., "Histogram of radon transform, a useful descriptor for shape retrieval," in 19th International Conference on Pattern Recognition (ICPR 2008), Dec. 8-11, 2008, Tampa, Florida, USA. IEEE Computer Society 2008, pp. 1-4.

Daras, et al., "Efficient 3-d model search and retrieval using generalized 3-d radon transforms," Multimedia, IEEE Transactions on, vol. 8(1), pp. 101-114, 2006.

Kadyrov, et al., "The trace transform and its applications," IEEE Trans, on Pattern Analysis and Machine Intell. vol. 23, No. 8, pp. 811-828, 2001.

Heutte, et al., "A structural/statistical feature based vector for handwritten character recognition," Pattern Recognition Letter, vol. 19, No. 7, pp. 629-641, 1998.

Jafari-Khouzani et al., "Radon transform orientation estimation for rotation invariant texture analysis," IEEE Transactions on Pattern Analysis and Machine Intelligence, vol. 27, No. 6, pp. 1004-1008, 2005.

Tizhoosh, "Barcode annotations for medical image retrieval: A preliminary investigation," in Image Processing (ICIP), 2015 IEEE International Conference on, pp. 818-822, Sep. 27-30, 2015, Quebec City, Quebec, CA.

Tizhoosh, et al., "MinMax Radon Barcodes for Medical Image Retrieval," Springer International Publishing, 2016, pp. 617-627.

Babaie et al., "Classification and retrieval of digital pathology scans: A new dataset," in Workshop for Computer Vision for Microscopy Image Analysis (CVMI 2017), CVPR, Jul. 21-26, 2017, Honolulu, Hawaii, USA.

(56) References Cited

OTHER PUBLICATIONS

Babaie et al., "Local Radon Descriptors for Image Search," 7th Int. Conf. on Image Processing Theory, Tools and Applications (IPTA 2017), Nov. 28-Dec. 1, 2017, Montreal, Quebec, CA.
Rajendran, et al., "Radon Transform based Local Tomography Algorithm for 3D Reconstruction,"Int'l Journal of Biology and Biomedical Eng., Issue 1, vol. 6, pp. 1-8, 2012.
Babaie, et al., "Retrieving Similar X-Ray Images from Big Image Data using Radon Barcodes with Single Projections," Proc. 6th Int'l. Conf. on Pattern Recognition Applications and Methods (ICPRAM) 2017), pp. 557-566, Feb. 24-26, 2017, Porto, Portugal.
Daugman, "How iris recognition works", IEEE Transactions on Circuits and Systems for Video Technology, Jan. 2004, vol. 14 (1), pp. 21-30.
Leutenegger et al., "Brisk: Binary Robust Invariant Scalable Key Points", in Proceedings of the 2011 IEEE International Conference on Computer Vision, Nov. 6-13, 2011, pp. 2548-2555.
Muja et al., "Fast Matching Of Binary Features," in Proceedings of the 2012 Ninth Conference on Computer and Robot Vision, May 28-30, 2012, CRV '12, pp. 404-410.
Nacereddine et al., "Shape-Based Image Retrieval Using A New Descriptor Based On The Radon And Wavelet Transforms", in International Conference on Pattern Recognition, Aug. 23-26, 2010, pp. 1197-2000.
Ojala et al., "MultiResolution Gray-Scale and Rotation invariant Texture Classification with Local Binary Patterns," IEEE Transactions on Pattern Analysis & Machine Intelligence, Aug. 7, 2002, vol. 24 (7), pp. 971-987.
Seoa et al., "A robust image fingerprinting using the Radon transform", Department of EECS, KAIST, 373-1 Guseong Dong, Yuseong Gu, Daejeon 305-701, South Korea Philips Research Eindhoven, Prof. Holstlaan 4, Eindhoven 5656AA, The Netherlands; May 6, 2003.
Sundermeyer et al., "LSTM Neural Networks for Language Modeling", Human Language Technology and Pattern Recognition, Computer Science Department, RWTH Aschen University, Aachen, Germany.
Kieffer, et al,. (Nov. 2017). Convolutional neural networks for histopathology image classification: training vs. using pre-trained networks. In 2017 Seventh International Conference on Image Processing Theory, Tools and Applications (IPTA) (pp. 1-6). IEEE.
Hunt et al., "A Microdissection and Molecular Genotyping Assay to Confirm the Identity of Tissue Floaters in Paraffin-Embedded Tissue Blocks", Molecular Identification of Tissue Floaters, Arch Pathol Lab Med, vol. 127, Feb. 2003, pp. 213-217.
Lowe, "Object recognition from local scale-invariant features." Computer vision, 1999. The proceedings of the seventh IEEE international conference on. vol. 2. Ieee, 1999.
Kohonen, "The self-organizing map." Proceedings of the IEEE 78.9 (1990): 1464-1480.
Hartigan, et al., "Algorithm AS 136: A k-means clustering algorithm." Journal of the Royal Statistical Society. Series C (Applied Statistics) 28.1 (1979): 100-108.
Vinyals, et al., (2017). Show and tell: Lessons learned from the 2015 mscoco image captioning challenge. IEEE transactions on pattern analysis and machine intelligence, 39(4), 652-663.
Bayramoglu, N., Kannala, J., & Heikkilä, J. (Dec. 2016). Deep learning for magnification independent breast cancer histopathology image classification. In 2016 23rd International conference on pattern recognition (ICPR) (pp. 2440-2445). IEEE.
Liu, Y., Gadepalli, K., Norouzi, M., Dahl, G. E., Kohlberger, T., Boyko, A., . . . & Hipp, J. D. (2017). Detecting cancer metastases on gigapixel pathology images. arXiv preprint arXiv:1703.02442 (13 pages).
Sellaro, T. L., Filkins, R., Hoffman, C., Fine, J. L., Ho, J., Parwani, A. V., . . . & Montalto, M. (2013) Relationship between magnification and resolution in digital pathology systems. Journal of pathology informatics, 4 (5 pages).
Song, Y., Zhang, L., Chen, S., Ni, D., Lei, B., & Wang, T. (2015). Accurate segmentation of cervical cytoplasm and nuclei based on multiscale convolutional network and graph partitioning. IEEE Transactions on Biomedical Engineering, 62(10), 2421-2433.
Romo, D., García-Arteaga, J. D., Arbeláez, P., & Romero, E. (Mar. 2014). A discriminant multi-scale histopathology descriptor using dictionary learning. In Medical Imaging 2014: Digital Pathology (vol. 9041, p. 90410Q). International Society for Optics and Photonics (7 pages).
Doyle, S., Madabhushi, A., Feldman, M., & Tomaszeweski, J. (Oct. 2006). A boosting cascade for automated detection of prostate cancer from digitized histology. In International conference on medical image computing and computer-assisted intervention (pp. 504-511). Springer, Berlin, Heidelberg.
Tizhoosh, Hamid Reza, and Liron Pantanowitz "Artificial intelligence and digital pathology: Challenges and opportunities." Journal of pathology informatics 9 (2018) (16 pages).
Kumar, Meghana Dinesh, et al. "A comparative study of cnn, bovw and lbp for classification of histopathological images." 2017 IEEE Symposium Series on Computational Intelligence (SSCI). IEEE, 2017 (8 pages).
Babaie, Morteza, and Hamid R. Tizhoosh. "Deep Features for Tissue-Fold Detection in Histopathology Images." arXiv preprint arXiv:1903.07011 (2019) (9 pages).
Chenni, Wafa, et al. "Patch Clustering for Representation of Histopathology Images." arXiv preprint arXiv:1903.07013 (2019) (9 pages).
ISA/CA, International Search Report and Written Opinion of the ISA, dated Feb. 7, 2020, re PCT International Application No. PCT/CA2019/051573 (11 pages).
Mahmood, "Artificial Intelligence-Based Mitosis Detection in Breast Cancer Histopathology Images Using Faster R-CNN and Deep CNNs", J. Clin. Med. 2020, 9, 749.
Araujo, "Classification of breast cancer histology images using Convolutional Neural Networks", PLoS One:12(6):e0177544.
Extended European Search Report for European Patent Application No. 19881000.4, dated Oct. 21, 2022 (12 pages).
Barker Jocelyn et al: "Automated classification of brain tumor type in whole-slide digital pathology images using local representative tiles", Medical Image Analysis, vol. 30, Dec. 29, 2015 (Dec. 29, 2015), pp. 60-71.
Tizhoosh et al., "Artificial intelligence and digital pathology: Challenges and opportunities." Journal of pathology informatics 9 (2018) (16 pages).
Kumar, et al. "A comparative study of cnn, bovw and lbp for classification of histopathological images." 2017 IEEE Symposium Series on Computational Intelligence (SSCI). IEEE, 2017 (8 pages).

\* cited by examiner

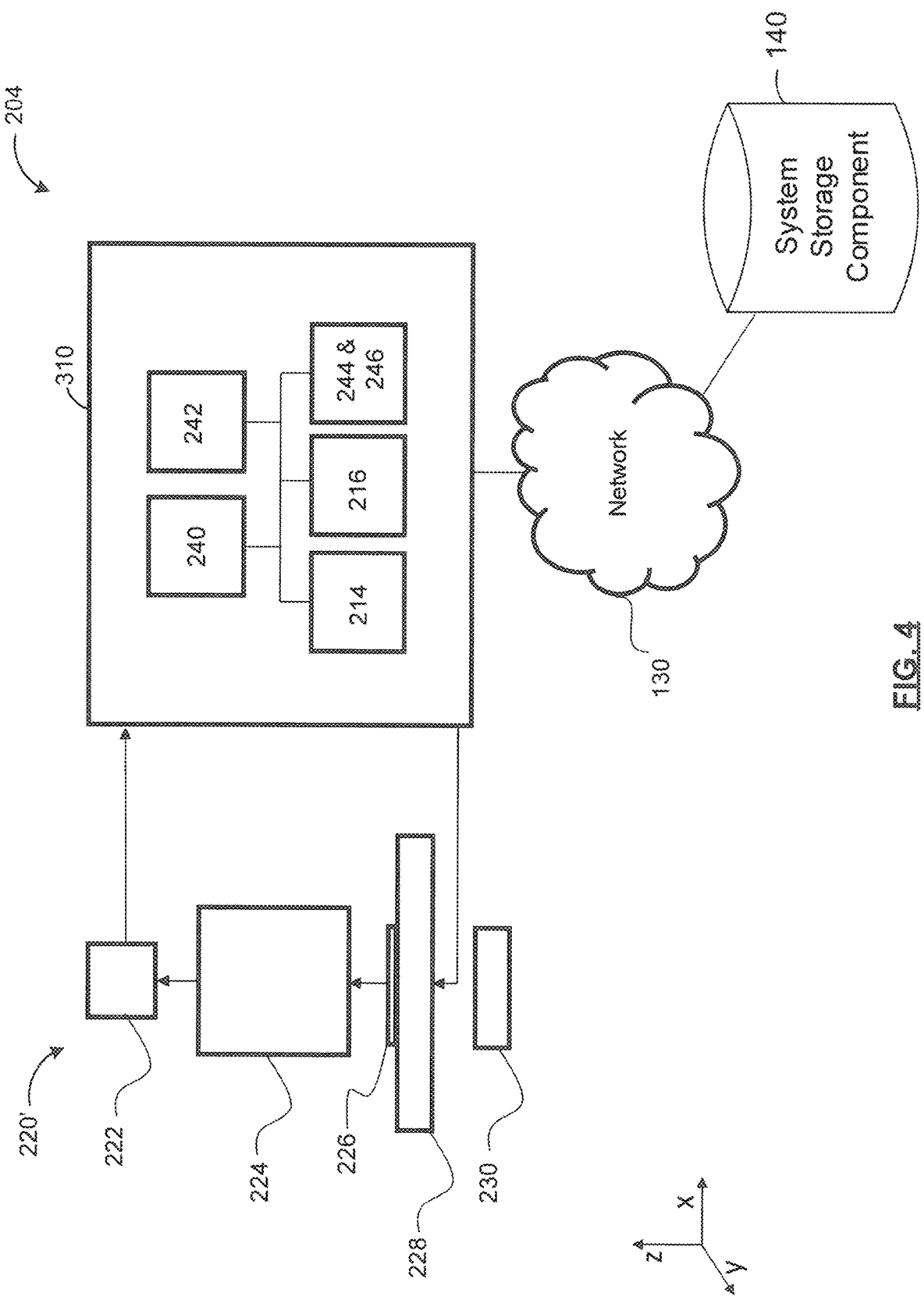

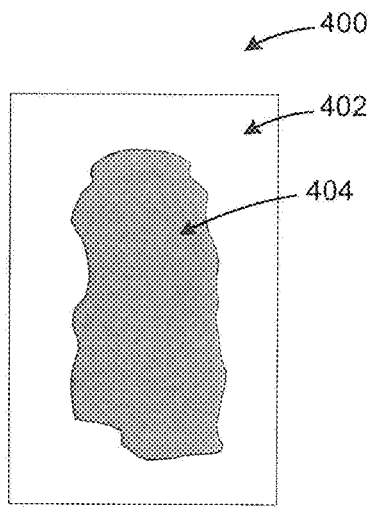
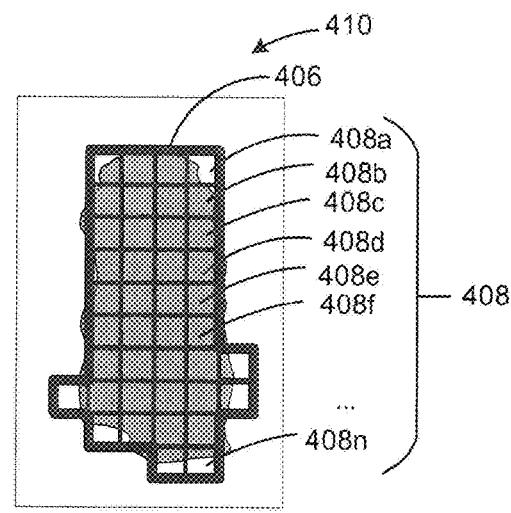
FIG. 9A          FIG. 9B
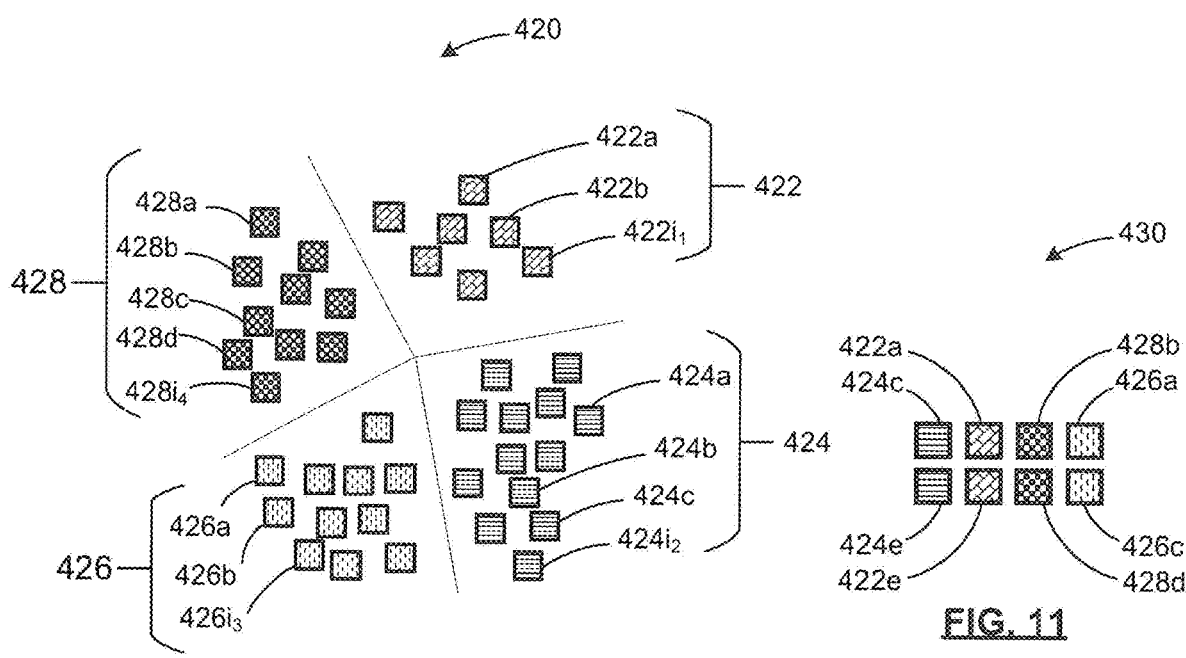
FIG. 10                    FIG. 11

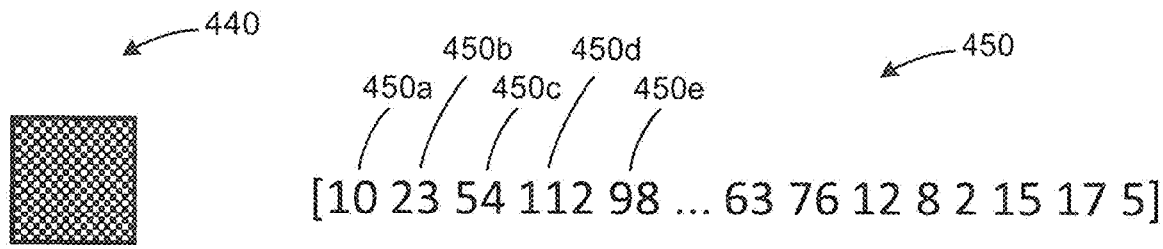
FIG. 12
FIG. 13
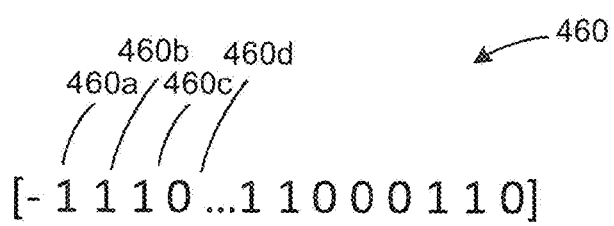
FIG. 14
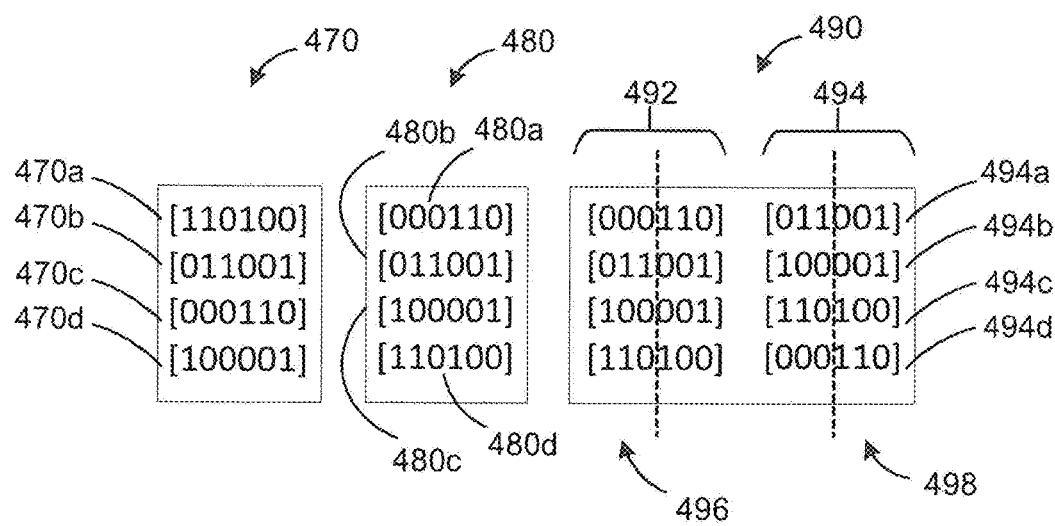
FIG. 15

SYSTEMS AND METHODS OF MANAGING MEDICAL IMAGES

CROSS-REFERENCE TO RELATED PATENT APPLICATION

The application claims the benefit of U.S. Provisional Application No. 62/755,862 filed on Nov. 5, 2018. The complete disclosure of U.S. Provisional Application No. 62/755,862 is incorporated herein by reference.

FIELD

The described embodiments relate to systems and methods of managing medical images and in particular, pathology-related images.

BACKGROUND

Digital images and videos are increasingly common forms of media. As more digital content is generated and becomes available, the usefulness of that digital content largely depends on its management.

Some existing practices involve associating the digital content with searchable descriptors. Although some of these descriptors may be automatically generated, these descriptors are typically generated based on features and/or qualities identified from human observations and judgement. In addition to the amount of time required for a human to observe and generate descriptive descriptors for the digital content, the descriptors may not be universal or adaptable between different systems. Also, existing descriptors can be limited by the extent in which the digital content can be processed.

SUMMARY

The various embodiments described herein generally relate to methods (and associated systems configured to implement the methods) for managing one or more images.

An example method involves operating a processor to, divide an image portion of an image of the one or more images into a plurality of patches and, for each patch of the image: detect one or more features of the patch; and assign the patch to at least one cluster of a plurality of clusters of the image, based on the one or more features of the patch. The method also involves operating the processor to, for each cluster of the image, select at least one patch from the cluster as at least one representative patch for the cluster; for each representative patch of the image, generate an encoded representation based on one or more features of the representative patch; and generate an index identifier for the image based on the encoded representations of the representative patches of the image.

In some embodiments, the method can also involve receiving a selected portion of the image as the image portion.

In some embodiments, the method can also involve receiving the image and extracting the image portion from the image.

In some embodiments, extracting the image portion from the image can involve segmenting a foreground of the image from a background of the image; and providing the foreground of the image as the image portion.

In some embodiments, a dimension of each patch can be predefined.

In some embodiments, a dimension of each patch can be characterized by a substantially similar number of pixels.

In some embodiments, each patch can be characterized by a square shape.

In some embodiments, the one or more features of the patch can include at least one of a structure and a color.

In some embodiments, assigning the patch to at least one cluster of the plurality of clusters can involve assigning the patch to one cluster of the plurality of clusters.

In some embodiments, detecting one or more features of the patch can include using at least one of a shift-invariant feature transform (SIFT), local binary pattern (LBP), encoded local projection (ELP), and deep features of an artificial neural network.

In some embodiments, assigning the patch to at least one cluster of the plurality of clusters of the image comprises using k-means.

In some embodiments, the plurality of clusters of the image can be predefined.

In some embodiments, assigning the patch to at least one cluster of the plurality of clusters of the image, based on the one or more features of the patch can involve determining a number of the plurality of clusters of the image based on a Self-Organizing Map.

In some embodiments, the plurality of clusters can include a first cluster and a second cluster; and, for each cluster of the image, selecting at least one patch from the cluster as at least one representative patch for the cluster can involve selecting an unequal number of representative patches for the first cluster and the second cluster.

In some embodiments, selecting an unequal number of representative patches can be based on a number of patches assigned to the cluster and a variation in image data of patches assigned to the cluster.

In some embodiments, generating the encoded representation can involve using at least one of a shift-invariant feature transform (SIFT), local binary pattern (LBP), encoded local projection (ELP), and deep features of an artificial neural network.

In some embodiments, generating the encoded representation can further involve using at least one of a minimum-maximum method and a thresholding method to convert a non-binary encoded representation to a binary encoded representation.

In some embodiments, generating an index identifier for the image based on the encoded representations of the representative patches of the image can involve sorting at least a portion of the encoded representations of the representative patches of the image to provide at least one ordered set of the encoded representations of the representative patches of the image as the index identifier for the image.

In some embodiments, sorting at least a portion of the encoded representations of the representative patches of the image can involve: sorting first portions of the encoded representations of the representative patches of the image to provide a first ordered set of the encoded representations; sorting second portions of the encoded representations of the representative patches of the image to provide a second ordered set of the encoded representations; and providing the first ordered set and the second ordered as the index for the image.

In some embodiments, the image can be a medical image.

In some embodiments, the method can involve searching a plurality of stored index identifier for analogous images based on the index identifier.

In some embodiments, searching the plurality of stored index identifiers for analogous images based on the index identifier can involve determining a measure of similarity between the index identifier and each of the plurality of stored index identifiers.

In some embodiments, the measure of similarity can be a Hamming distance. For example, determining the measure of similarity between the index identifier and each of the plurality of stored index identifiers can involve determining a Hamming distance between the index identifier and each of the plurality of stored index identifiers.

In some embodiments, the method can involve operating the processor to pre-process the one or more images prior to dividing the image portion of the image of the one or more images into a plurality of patches.

In another broad aspect, a method of retrieving for one or more images is disclosed herein. The method involves operating a processor to, divide at least a portion of a query image into a plurality of patches; for each patch of the query image, detect one or more features of the patch; generate an encoded representation based on one or more features of the patches; generate an index identifier for the query image based on the encoded representations of the patches; compare the index identifier to a plurality of stored index identifiers to locate one or more analogous images; and retrieve the one or more analogous images.

In some embodiments, the method can involve determining whether the query image relates to an entire image or a region of interest of the entire image. In response to determining that the query image relates to a region of interest of the entire image, dividing at least a portion of the query image can involve dividing the region of interest into the plurality of patches. In response to determining that the query image relates to the entire image: extracting an image portion from the image and dividing the image portion into the plurality of patches; for each patch of the query image, detecting one or more features of the patch and assigning the patch to at least one cluster of a plurality of clusters of the query image, based on the one or more features of the patch; for each cluster of the query image, selecting at least one patch from the cluster as at least one representative patch for the cluster; detecting one or more features of the representative patch; and generating an encoded representation based on one or more features of the patches comprises generating the encoded representation based on one or more features of the representative patches.

In some embodiments, comparing the index identifier to the plurality of stored index identifiers can include determining a measure of similarity between the index identifier and each of the plurality of stored index identifiers. For example, determining the measure of similarity between the index identifier and each of the plurality of stored index identifiers can include determining a Hamming distance between the index identifier and each of the plurality of stored index identifiers.

In some embodiments, retrieving the one or more analogous images can involve retrieving a predefined number of images having highest measures of similarity.

In some embodiments, retrieving the one or more analogous images can involve retrieving the one or more analogous images having a measure of similarity greater than a predefined threshold.

In some embodiments, the method can involve for each analogous image: detecting one or more features of the analogous image; determining a measure of similarity between the features of the analogous images and features of the patches of the query image; and sorting the one or more analogous images based on the measures of similarity between the features of the analogous images and features of the patches of the query image.

In some embodiments, the measure of similarity can be at least one of a Euclidean distance, chi-square distance, and cosine similarity.

In some embodiments, the method can involve automatically generating a report for the query image based on the retrieved one or more analogous images.

In some embodiments, the processor can include a device processor and a management processor remote to the device processor and operable to be in communication with the device processor, and the method can involve: operating the device processor to: divide the at least the portion of the query image into the plurality of patches; for each patch of the query image, detect the one or more features of the patch; generate the encoded representation based on the one or more features of the patches; generate the index identifier for the query image based on the encoded representations of the patches; transmit the index identifier to the management processor; and operating the management processor to: compare the index identifier to the plurality of stored index identifiers to locate one or more analogous images; and retrieve the one or more analogous images.

In some embodiments, the method can involve operating the device processor to transmit the index identifier to the management processor via a network.

In some embodiments, the method can involve operating the device processor to pre-process the query image prior to dividing the at least the portion of the query image into the plurality of patches.

In another broad aspect, a system for indexing for one or more images is disclosed herein. The system can include a communication component and a processor in communication with the communication component. The communication component can provide access to the one or more images via a network. The processor can be operable to, divide an image portion of an image of the one or more images into a plurality of patches; and for each patch of the image: detect one or more features of the patch; and assign the patch to at least one cluster of a plurality of clusters of the image, based on the one or more features of the patch. The processor can be operable to, for each cluster of the image, select at least one patch from the cluster as at least one representative patch for the cluster; for each representative patch of the image, generate an encoded representation based on one or more features of the representative patch; and generate an index identifier for the image based on the encoded representations of the representative patches of the image.

In some embodiments, the processor can be operable to receive a selected portion of the image as the image portion.

In some embodiments, the processor can be operable to receive the image and extract the image portion from the image.

In some embodiments, the processor can be operable to: segment a foreground of the image from a background of the image; and provide the foreground of the image as the image portion.

In some embodiments, a dimension of each patch can be predefined.

In some embodiments, a dimension of each patch can be characterized by a substantially similar number of pixels.

In some embodiments, each patch can be characterized by a square shape.

In some embodiments, the one or more features of the patch can include at least one of a structure and a color.

In some embodiments, the processor can be operable to assign the patch to one cluster of the plurality of clusters.

In some embodiments, the processor can be operable to use at least one of a shift-invariant feature transform (SIFT), local binary pattern (LBP), encoded local projection (ELP), and deep features of an artificial neural network to detect one or more features of the patch.

In some embodiments, the processor can be operable to use k-means to assign the patch to at least one cluster of the plurality of clusters of the image.

In some embodiments, the plurality of clusters of the image can be predefined.

In some embodiments, the processor can be operable to determine a number of the plurality of clusters of the image based on a Self-Organizing Map.

In some embodiments, the plurality of clusters can include a first cluster and a second cluster; and the processor can be operable to select an unequal number of representative patches for the first cluster and the second cluster.

In some embodiments, the processor can be operable to select an unequal number of representative patches can be based on a number of patches assigned to the cluster and a variation in image data of patches assigned to the cluster.

In some embodiments, the processor can be operable to use at least one of a shift-invariant feature transform (SIFT), local binary pattern (LBP), encoded local projection (ELP), and deep features of an artificial neural network to generate the encoded representation.

In some embodiments, the processor can be operable to use at least one of a minimum-maximum method and a thresholding method to convert a non-binary encoded representation to a binary encoded representation.

In some embodiments, the processor can be operable to sort at least a portion of the encoded representations of the one or more representative patches for the image to provide at least one ordered set of the encoded representations of the one or more representative patches for the image as the index identifier for the image.

In some embodiments, the processor can be operable to sort first portions of the encoded representations of the representative patches of the image to provide a first ordered set of the encoded representations; sort second portions of the encoded representations of the representative patches of the image to provide a second ordered set of the encoded representations; and provide the first ordered set and the second ordered as the index identifier for the image.

In some embodiments, the image can be a medical image.

In some embodiments, the processor can be operable to search a plurality of stored index identifiers for analogous images based on the index identifier.

In some embodiments, the processor can be operable to determine a measure of similarity between the index and each of the plurality of stored index identifiers.

In some embodiments, the measure of similarity can be a Hamming distance. For example, the processor can operate to determine the measure of similarity by determining a Hamming distance between the index identifier and each of the plurality of stored index identifiers.

In some embodiments, the processor can operate to pre-process the one or more images prior to dividing the image portion of the image of the one or more images into a plurality of patches.

In another broad aspect, a system for retrieving for one or more images is disclosed herein. The system can include a communication component and a processor in communication with the communication component. The communication component can provide access to the one or more images via a network. The processor can be operable to, divide at least a portion of a query image into a plurality of patches; for each patch of the query image, detect one or more features of the patch; generate an encoded representation based on one or more features of the patches; generate an index identifier for the query image based on the encoded representations of the patches; compare the index identifier to a plurality of stored index identifiers to locate one or more analogous images; and retrieve the one or more analogous images.

In some embodiments, the processor can be operable to determine whether the query image relates to an entire image or a region of interest of the entire image. In response to determining that the query image relates to a region of interest of the entire image, the processor can be operable to divide the region of interest into the plurality of patches. In response to determining that the query image relates to the entire image, the processor can be operable to: extract an image portion from the image and divide the image portion into the plurality of patches; for each patch of the query image, detect one or more features of the patch and assign the patch to at least one cluster of a plurality of clusters of the query image, based on the one or more features of the patch; for each cluster of the query image, select at least one patch from the cluster as at least one representative patch for the cluster; detect one or more features of the representative patches; and generate an encoded representation based on one or more features of the representative patches.

In some embodiments, the processor can be operable to determine a measure of similarity between the index identifier and each of the plurality of stored index identifiers to compare the index identifier to the plurality of stored index identifiers.

In some embodiments, the measure of similarity can be a Hamming distance. For example, the processor can operate to determine the measure of similarity by determining a Hamming distance between the index identifier and each of the plurality of stored index identifiers.

In some embodiments, the processor can be operable to retrieve a predefined number of images having highest measures of similarity.

In some embodiments, the processor can be operable to retrieve the one or more analogous images having a measure of similarity greater than a predefined threshold.

In some embodiments, the processor can be further operable to: for each analogous image, detect one or more features of the analogous image; determine a measure of similarity between the features of the analogous images and features of the patches of the query image; and sort the one or more analogous images based on the measures of similarity between the features of the analogous images and features of the patches of the query image.

In some embodiments, the measure of similarity can be at least one of a Euclidean distance, chi-square distance, and cosine similarity.

In some embodiments, the processor can operate to automatically generate a report for the query image based on the retrieved one or more analogous images.

In some embodiments, the processor can include a device processor and a management processor remote to the device processor and operable to be in communication with the device processor, and the device processor can be operable to: divide the at least the portion of the query image into the plurality of patches; for each patch of the query image, detect the one or more features of the patch; generate the encoded representation based on the one or more features of the patches; and generate the index identifier for the query image based on the encoded representations of the patches; and the management processor is operable to: receive the index identifier from the device processor; compare the index identifier to the plurality of stored index identifiers to locate one or more analogous images; and retrieve the one or more analogous images.

In some embodiments, the device processor can be operable to transmit the index identifier to the management processor via a network.

In some embodiments, the device processor can be operable to pre-process the query image prior to dividing the at least the portion of the query image into the plurality of patches.

In another broad aspect, a method of managing one or more medical query images is disclosed herein. The method can involve operating a device processor to: for each medical query image, detect one or more features within the medical query image; generate at least one encoded representation for each medical query image based on the respective detected one or more features; generate an index identifier for each medical query image based on the at least one encoded representation; and operating a management processor remote from the device processor to: receive the index identifier from the device processor; compare the index identifier with a plurality of stored index identifiers to locate one or more analogous images; and retrieve the one or more analogous images.

In some embodiments, generating the at least one encoded representation can involve using at least one of a minimum-maximum method and a thresholding method to convert a non-binary encoded representation to a binary encoded representation.

In some embodiments, comparing the index identifier with the plurality of stored index identifiers to locate the one or more analogous images can involve determining a measure of similarity between the index identifier and each index identifier of the plurality of stored index identifiers.

In some embodiments, determining the measure of similarity between the index identifier and each of the plurality of stored index identifiers can involve determining a Hamming distance between the index identifier and each of the plurality of stored index identifiers.

In some embodiments, the method can involve operating the device processor to pre-process each medical query image prior to detecting the one or more features within the respective query image.

In some embodiments, retrieving the one or more analogous images can involve retrieving a predefined number of images having highest measures of similarity.

In some embodiments, retrieving the one or more analogous images can involve retrieving the one or more analogous images having a measure of similarity greater than a predefined threshold.

In some embodiments, the method can involve: for each analogous image: detecting one or more features of the analogous image; determining a measure of similarity between the one or more features of the analogous images and the one or more features of each respective medical query image; and sorting the one or more analogous images based on the measure of similarity between each of the one or more features of the analogous images and the one or more features of each respective medical query image.

In some embodiments, the measure of similarity can involve at least one of a Euclidean distance, chi-square distance, and cosine similarity.

In some embodiments, the method can involve automatically generating a report for the medical query image based on the retrieved one or more analogous images.

In some embodiments, the method can involve operating the device processor to transmit the index identifier to the management processor via a network.

In a broad aspect, a system for managing one or more medical query images is disclosed herein. The system can include a device processor operable to: for each medical query image, detect one or more features within the medical query image; generate at least one encoded representation for each medical query image based on the respective detected one or more features; generate an index identifier for each medical query image based on the at least one encoded representation; and a management processor remote from the device processor, the management processor operable to: receive the index identifier from the device processor; compare the index identifier with a plurality of stored index identifiers to locate one or more analogous images; and retrieve the one or more analogous images.

In some embodiments, the device processor is operable to use at least one of a minimum-maximum method and a thresholding method to convert a non-binary encoded representation to a binary encoded representation.

In some embodiments, the management processor is operable to determine a measure of similarity between the index identifier and each index identifier of the plurality of stored index identifiers.

In some embodiments, the management processor is operable to determine a Hamming distance between the index identifier and each of the plurality of stored index identifiers as the measure of similarity.

In some embodiments, the device processor is operable to pre-process each medical query image prior to detecting the one or more features within the respective query image.

BRIEF DESCRIPTION OF THE DRAWINGS

Several embodiments will now be described in detail with reference to the drawings, in which:

FIG. 4 is a block diagram of another example image management system;

FIG. 9A is an example of an image;

FIG. 9B is an example plurality of patches of the image of FIG. 9A;

FIG. 10 is a schematic illustrating an example assignment of a plurality of patches to a plurality of clusters of the image of FIG. 9A;

FIG. 11 is a schematic illustrating example representative patches of the image of FIG. 9A;

FIG. 12 is an example representative patch of the image of FIG. 9A;

FIG. 13 is an example encoded representation of the representative patch of FIG. 12;

FIG. 14 is an example binary encoded representation of the representative patch of FIG. 12;

FIG. 15 are schematics illustrating unsorted and sorted sets of encoded representations;

Figure 1:
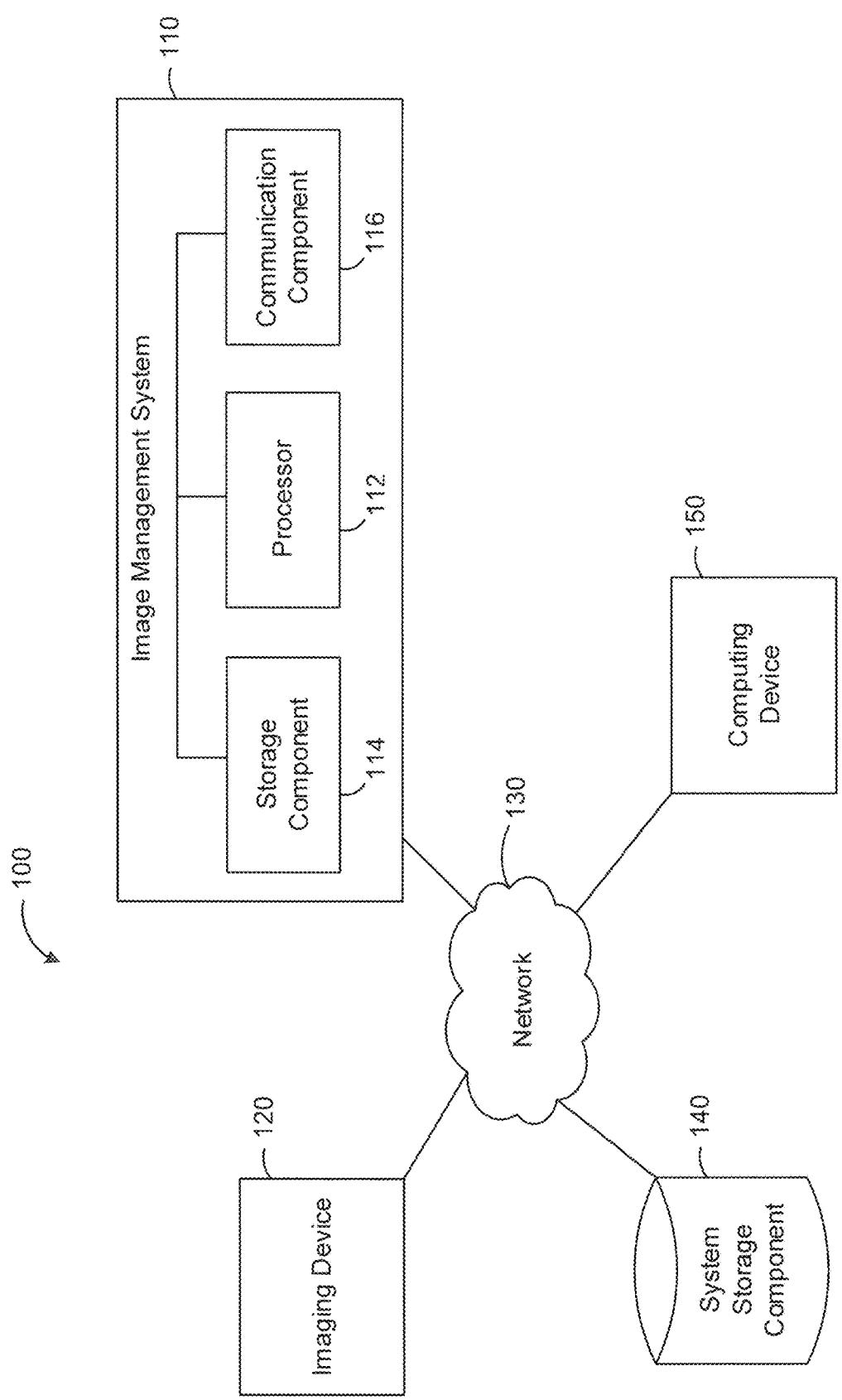
FIG. 1 is a block diagram of an image management system, in accordance with an example embodiment.

The drawings, described below, are provided for purposes of illustration, and not of limitation, of the aspects and features of various examples of embodiments described herein. For simplicity and clarity of illustration, elements shown in the drawings have not necessarily been drawn to scale. The dimensions of some of the elements may be exaggerated relative to other elements for clarity. It will be appreciated that for simplicity and clarity of illustration, where considered appropriate, reference numerals may be repeated among the drawings to indicate corresponding or analogous elements or steps.

DESCRIPTION OF EXAMPLE EMBODIMENTS

The various embodiments described herein generally relate to methods (and associated systems configured to implement the methods) for indexing one or more images, and/or searching for one or more images.

Existing practices involve associating images with image descriptors that are searchable to assist with the management of the image data. Keyword or tag descriptor-based approaches require manual human annotation and judgement, which can be impractical in view of the large amount of image and video data that typically needs to be processed.

Although some of these descriptors may be automatically generated, these descriptors are typically generated based on features and/or qualities identified from human observations and judgement. In addition to the amount of time required for a human to observe and generate descriptive descriptors for the digital content, the descriptors may not be universal or adaptable between different systems.

In many image processing systems, the quality of the descriptors can be limited by the computer resources. Depending on the resolution of an image, existing image descriptors may be insufficient to accurately identify similar images. Existing image descriptors can be complex and involve computationally intensive calculations. The computational power may not readily be available and/or insufficient to handle the growing amount of digital content being generated. As well, the existing image descriptors can require large amount of storage capacity, which results in additional cost or may not be available at all.

In the medical field, for example, medical images of patients are regularly captured for diagnostic and/or monitoring purposes. Medical images can be generated by many different imaging devices and undergo visual or numerical investigation for medical diagnoses and research. These medical images are typically archived and may be retrieved for a later purpose (e.g., research or educational). Timely and consistent representation of these images can likely assist with diagnosis. Similarly, many other sectors, such as architectural and engineering design, geoinformatics, museum and gallery collections, retail catalogs, material processing, military and defense applications, surveillance and forensics, can also benefit from efficient and consistent management of image data.

The ability to efficiently and consistently index images, and retrieve those images can be advantageous for these sectors. For example, in the medical field, as medical images are analyzed for a medical diagnosis, the medical images can be compared with archived images of diagnosed cases to assist with the diagnosis. Also, the present diagnosis can benefit from archived images, which may have been clinically evaluated and annotated for second opinions, research, or educational purposes. Existing image descriptors can facilitate the retrieval of archived images and the retrieval of similar images but the image descriptors may be inconsistent between medical facilities and equipment.

Index identifiers of images generated in accordance with the methods and systems described herein can classify the images consistently. The index identifiers can then be used to identify analogous images and/or analogous portions of images for comparison. Furthermore, the comparison can assist in the identification of artifacts within images and generation of image caption data.

The index identifiers generated from the methods and systems disclosed herein can be applied in content-based image retrieval (CBIR) methods.

Reference is first made to FIG. 1, which illustrates an example block diagram 100 of an image management system 110 in communication with an imaging device 120, a system storage component 140, and a computing device 150 via a network 130. Although only one imaging device 120 and one computing device 150 are shown in FIG. 1, the image management system 110 can be in communication with include fewer or more imaging devices 120 and fewer or more computing devices 150. The image management system 110 can communicate with the devices 120, 150 over a wide geographic area via the network 130.

The imaging device 120 can include any device capable of capturing image data and/or generating images, and/or storing image data.

As shown in FIG. 1, the image management system 110 includes a processor 112, a storage component 114, and a communication component 116. The image management system 110 may include one or more servers that may be distributed over a wide geographic area and connected via the network 130. In some embodiments, each of the processor 112, the storage component 114 and the communication component 116 may be combined into a fewer number of components or may be separated into further components.

The processor 112 may be any suitable processors, controllers, digital signal processors, graphics processing units, application specific integrated circuits (ASICs), and/or field programmable gate arrays (FPGAs) that can provide sufficient processing power depending on the configuration, purposes and requirements of the image management system 110. In some embodiments, the processor 112 can include more than one processor with each processor being configured to perform different dedicated tasks.

The processor 112 may be configured to control the operation of the image management system 110. The processor 112 can include modules that initiate and manage the operations of the image management system 110. The processor 112 may also determine, based on received data, stored data and/or user preferences, how the image management system 110 may generally operate.

When the index identifiers disclosed herein are generated, the associated images are encoded. The index identifier represents a content of the image. In this way, the indexed image can be searched. A database of indexed images, or of links to indexed images, can be used in the image management system 110 to compare and retrieve similar or related images.

When indexing an image, the processor 112 can populate the storage component 114 or the system storage component 140 with the image. For example, the communication component 116 can receive the image from the imaging device 120. The processor 112 can then process the image according to the methods described herein. The processor 112 can generate an index identifier for the image and store the index identifier. In some embodiments, the index identifier may be embedded as metadata in the image file.

When searching for an image and retrieving the image, the processor 112 can generate an image query based on the index identifier and trigger a search for the associated image in the storage component 114 or the system storage component 140. The image query generated by the processor 112 can search the storage component 114 or the system storage component 140 for similar index identifiers. The retrieved similar index identifiers can direct the processor 112 to the related images and/or reports associated with the related images stored in the storage component 114 or in the system storage component 140. The processor 112 can retrieve the related image and/or associated report with an image query search, for example.

A degree of similarity between index identifiers can be determined by comparing the bit values between the index identifiers. In some embodiments, a degree of similarity between the index identifiers may be determined with a Hamming distance calculation.

The image(s) associated with the similar stored index identifiers is useful to the user running the image query search on the image management system 110. In the medical imaging context, a medical professional (radiologist, pathologist, diagnostician, researcher, etc.) may scan a patient and use the image to search for more information about the patient's illness.

For example, the processor 112 can receive an image query that defines a size, shape, and location of a tumor. In some embodiments, the image query can originate from the computing device 150. The processor 112 can then trigger a search for images that satisfy that image query. When the image management system 110 receives the search results, the communication component 116 can display the resulting images to the user for review. In some embodiments, the resulting images can be displayed at the computing device 150. The image management system 110 can provide further information in respect to each of the results for the user, such as the medical case information of each result. Accordingly, the user can see how previous patients with a similar tumor were diagnosed, treated and evaluated.

The communication component 116 may be any interface that enables the image management system 110 to communicate with other devices and systems. In some embodiments, the communication component 116 can include at least one of a serial port, a parallel port or a USB port. The communication component 116 may also include at least one of an Internet, Local Area Network (LAN), Ethernet, Firewire, modem, fiber, or digital subscriber line connection. Various combinations of these elements may be incorporated within the communication component 116.

For example, the communication component 116 may receive input from various input devices, such as a mouse, a keyboard, a touch screen, a thumbwheel, a track-pad, a track-ball, a card-reader, voice recognition software and the like depending on the requirements and implementation of the image management system 110.

The storage component 114 can include RAM, ROM, one or more hard drives, one or more flash drives or some other suitable data storage elements such as disk drives, etc. The storage component 114 is used to store an operating system and programs, for example. For instance, the operating system provides various basic operational processes for the processor. The programs include various user programs so that a user can interact with the processor to perform various functions such as, but not limited to, viewing and/or manipulating the image data as well as retrieving and/or transmitting image data as the case may be.

In some embodiments, the storage component 114 can store the images, information related to index identifiers of the images, and information related to the imaging devices 120.

The storage component 114 may include one or more databases (not shown) for storing image data, information relating to the image data, such as, for example, patient data with respect to the image data, and information related to reports associated with the images, such as, for example, diagnoses with respect to the image data. For example, the storage component 114 can store indices generated by the methods and systems described herein. Each index can also be associated with additional information on the tissue type, cancer type, etc., and can be accompanied by relevant pathology reports. When a search conducted by the image management system 110 identifies an index with associated reports, a later review of the initial query image by the pathologist can benefit from the associated reports.

Similar to the storage component 114, the system storage component 140 can store images and information related to images. Images and information related to images can be stored in the system storage component 140 for retrieval by the computing device 150 or the image management system 110.

Images described herein can include any digital image with any number of pixels. The images can have any size and resolution. In some embodiments, the size and resolution of the image can be adjusted in one or more pre-processing stages. Example image pre-processing includes normalizing the pixel dimensions of an image and digital filtering for noise reduction.

An example image is a medical image of a body part, or part of a body part. A medical image can be generated using any modality, including but not limited to microscopy, X-ray radiography, magnetic resonance imaging (MRI), ultrasound, and/or computed tomography scans (CT scans). Microscopy can include, but is not limited to whole slide imaging (WSI), reflected light, brightfield, transmitted light, fluorescence, and photoluminescence.

The image can be a black and white, grey-level, RGB color, or false color image. An image data structure typically includes an intensity value at each pixel location. To capture a wide dynamic range of intensity values, the data structure of the image uses a number of data bits to represent each pixel.

Sub-images, or patches, can also be defined within images. The dimensions of a patch are generally smaller than the dimensions of the image itself.

Information related to index identifiers of images that may be stored in the storage component 114 or the system storage component 140 may, for example, include but is not limited to the patches, features detected in the patches, clusters, representative patches of the clusters, features detected in the representative patches, encoded representations of the representative patches, including encoded representations containing integer values and/or binary values.

Information related to image annotations that may be stored in the storage component 114 or the system storage component 140 may, for example, include but is not limited to text comments, audio recordings, markers, shapes, lines, free form mark-ups, and measurements.

Information related to imaging devices that may be stored in the storage component 114 or the system storage component 140 may, for example, include but is not limited to a device identifier, a device location, a device operator, a modality, supported image resolutions, supported image file types, image size range, image margin ranges, and an image scale range.

Information related to image subjects that may be stored in the storage component 114 or the system storage component 140 may, for example, include but is not limited to a patient identifier, a date of birth, gender, home address, primary physician, and medical team in the case of medical images.

In some embodiments, the image management system 110 can receive images directly from the imaging device 120. For example, the image management system 110 can read images directly from a storage component of the imaging device 120. The image management system 110 may process query images, generate index identifiers, and retrieve similar images in real-time or nearly in real-time, as the query images are being received from the imaging device 120. By increasing the speed in which the query image can be reviewed and analyzed with respect to an archive of images in real-time, or near real-time, the disclosed image management system 110 can significantly improve patient care and responsiveness.

In the context of the present disclosure, the terms "real-time" or "near real-time" is defined as image processing that is concurrent to, or within a small temporal window of, the query image acquisition or generation. The purpose of real-time or near real-time image processing is to deliver search and retrieval results from the image management system 110 to the user within seconds or minutes after a medical imaging scan of the patient. Accordingly, related medical case information may be delivered to the patient's doctor with minimal delay, for a timely diagnosis of the patient's illness.

In some embodiments, images can be loaded into the image management system 110 from the system storage component 140 or computing device 150 that is remote from the image management system 110. For example, the image management system 110 may be used to process offsite data. Processing offsite data or non-time-sensitive data can assist with various applications, such as research applications where real-time processing (i.e., concurrent to image acquisition or generation) is not necessary, and/or medical diagnostic applications at areas (e.g., remote areas, underprivileged areas, underdeveloped areas, etc.) where real-time processing is not possible, or nearly impossible due to unreliable or slow communication networks. For research applications, a researcher tasked with processing hundreds or thousands of medical images would still benefit from the increased processing speed of the image management system 110 over conventional feature-based detection CBIR systems, even if the hundreds or thousands of medical images are not related to any patients awaiting diagnosis. In areas with unreliable and/or slow communication networks (e.g., remote areas, underprivileged areas, underdeveloped areas, etc.), the methods and systems described herein can facilitate searching of the image even with the unreliable and/or slow communication networks.

The computing device 150 may be any networked device operable to connect to the network 130. A networked device is a device capable of communicating with other devices through a network such as the network 130. A network device may couple to the network 130 through a wired or wireless connection.

The computing device 150 may include at least a processor and memory, and may be an electronic tablet device, a personal computer, workstation, server, portable computer, mobile device, personal digital assistant, laptop, smart phone, WAP phone, an interactive television, video display terminals, gaming consoles, and portable electronic devices or any combination of these.

In some embodiments, the computing device 150 may be a laptop, or a smartphone device equipped with a network adapter for connecting to the Internet. In some embodiments, the connection request initiated from the computing device 150 may be initiated from a web browser and directed at the browser-based communications application on the image management system 110.

The network 130 may be any network capable of carrying data, including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these, capable of interfacing with, and enabling communication between, the image management system 110, the imaging device 120, the system storage component 140, and the computing device 150.

Figure 2:
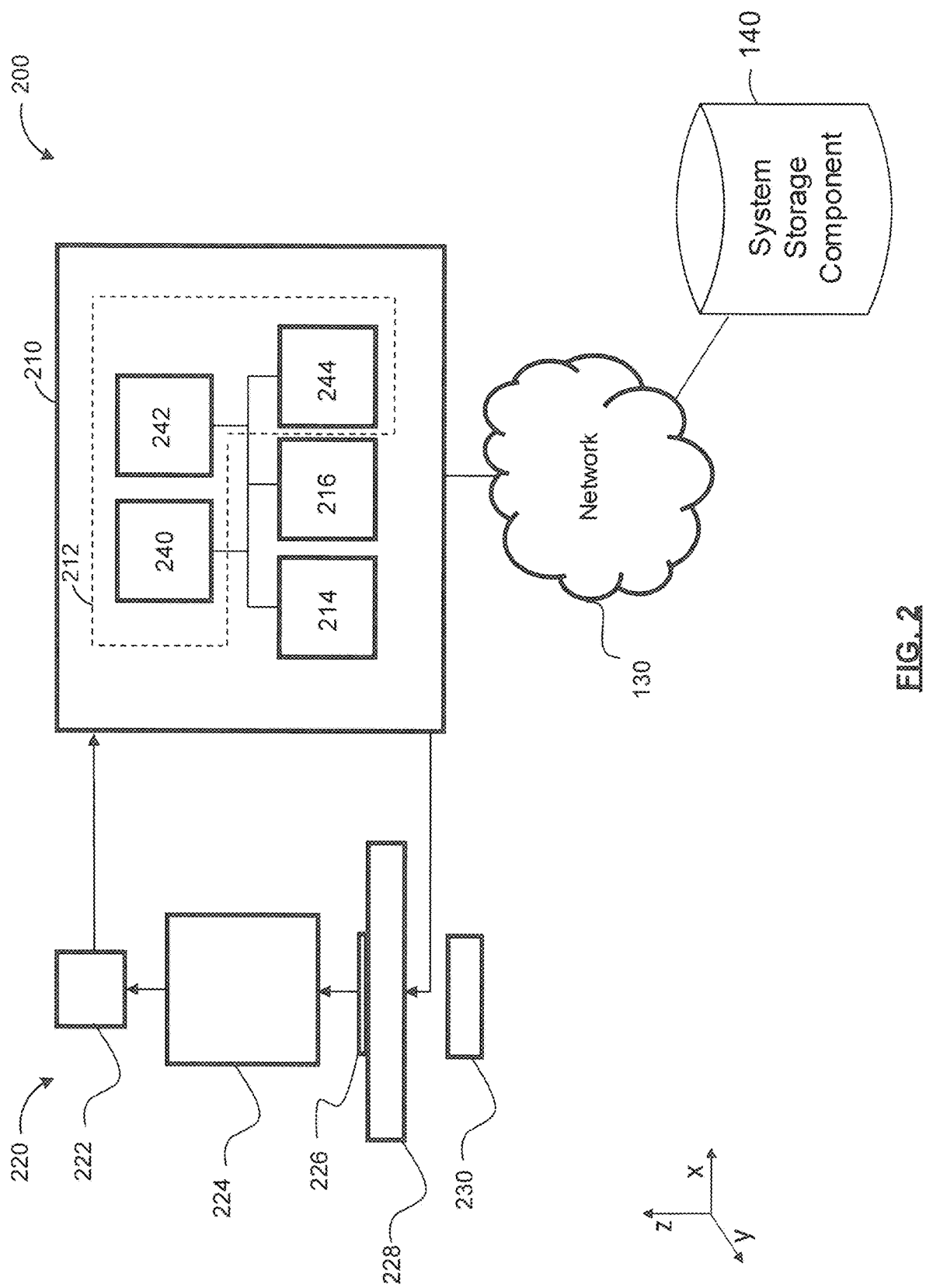
FIG. 2 is a block diagram of another example image management system.

Reference will be made to FIG. 2, which shows a block diagram 200 of an example image management system 210 in communication with an example imaging device 220, and the system storage component 140 via the network 130.

In the example shown in FIG. 2, the imaging device 220 includes a camera 222 positioned relative to a microscope 224. A slide 226 rests on a positioning stage 228 which can be illuminated by an illumination component 230. The positioning stage 228 and the illumination component 230 can, in some embodiments, be combined into one component. The positioning stage 228 can include an x-y stage. In some embodiments, the positioning stage 228 can be manually operated by the user to focus on specific areas of the slide. The operation of the positioning stage 228 and the area scan camera 222 can be controlled by the image management system 210.

In operation, the image management system 210 can operate the positioning stage 228 in an x-y direction in conjunction with the microscope 224 and the camera 222 for generating various image frames of the slide 226. Each frame can correspond to a different portion of the slide 226. The image management system 210 can capture an entire specimen via raster scanning the positioning stage 228. The image management system 210 can keep the specimen in focus by moving the objective in the z-direction (e.g., along the optic axis). In this example, the imaging device 220 is used to generate bright-field images.

The imaging device 220 can transmit the frames to the image management system 210 for processing.

Similar to FIG. 1, the image management system 210 shown in FIG. 2 can include a processor 212, a storage component 214 and a communication component 216. The processor 212 can pre-process the frames received from the image device 220, index the frames and/or the pre-processed frames, and/or search the storage component 214 and/or the system storage component 140 using the index generated by the processor 212. In FIG. 2, for illustrative purposes, the processor 212 is shown to include a pre-processing component 240, an indexing component 242, and a searching component 244. Although components 240, 242, 244 are shown as separate components in FIG. 2, the pre-processing component 240, the indexing component 242, and the searching component 244 can be combined into a fewer number of components or may be separated into further components, in some embodiments. Each of components 240, 242, 244 may also be implemented with hardware or software, or a combination of both. For example, components 240, 242, 244 can include computer programs executable by the processor 212 to conduct the relevant operations.

The pre-processing component 240, for example, can operate to stitch the frames received from the imaging device 220 together to produce a whole slide image representing the slide 226 entirely. The pre-processing component 240 can also, or alternatively, apply different processing techniques to the frames, including, but not limited to, field flattening, de-Bayering, sharpening, de-noising, color correction, and compression. The processor 212 can then store the whole slide image generated by the pre-processing component 240 into the storage component 214, for example.

The indexing component 242, as described herein, can operate to generate an index identifier to represent at least a portion of the frames (e.g., key features) and/or the whole image generated from the frames. The indexing component 242 can receive the frames directly from the imaging device 220—that is, the pre-processing component 240 can be optional.

The searching component 244 can operate to search the storage component 214 and/or the system storage component 140 using an image query based on the index identifier generated by the indexing component 242, as described herein. As the index identifier represents a portion of each of the frame or whole image, the index identifier includes less data than the complete frame or whole image. Searching with the index identifier can be faster than searching with the data associated with the complete frame or whole image.

Figure 3:
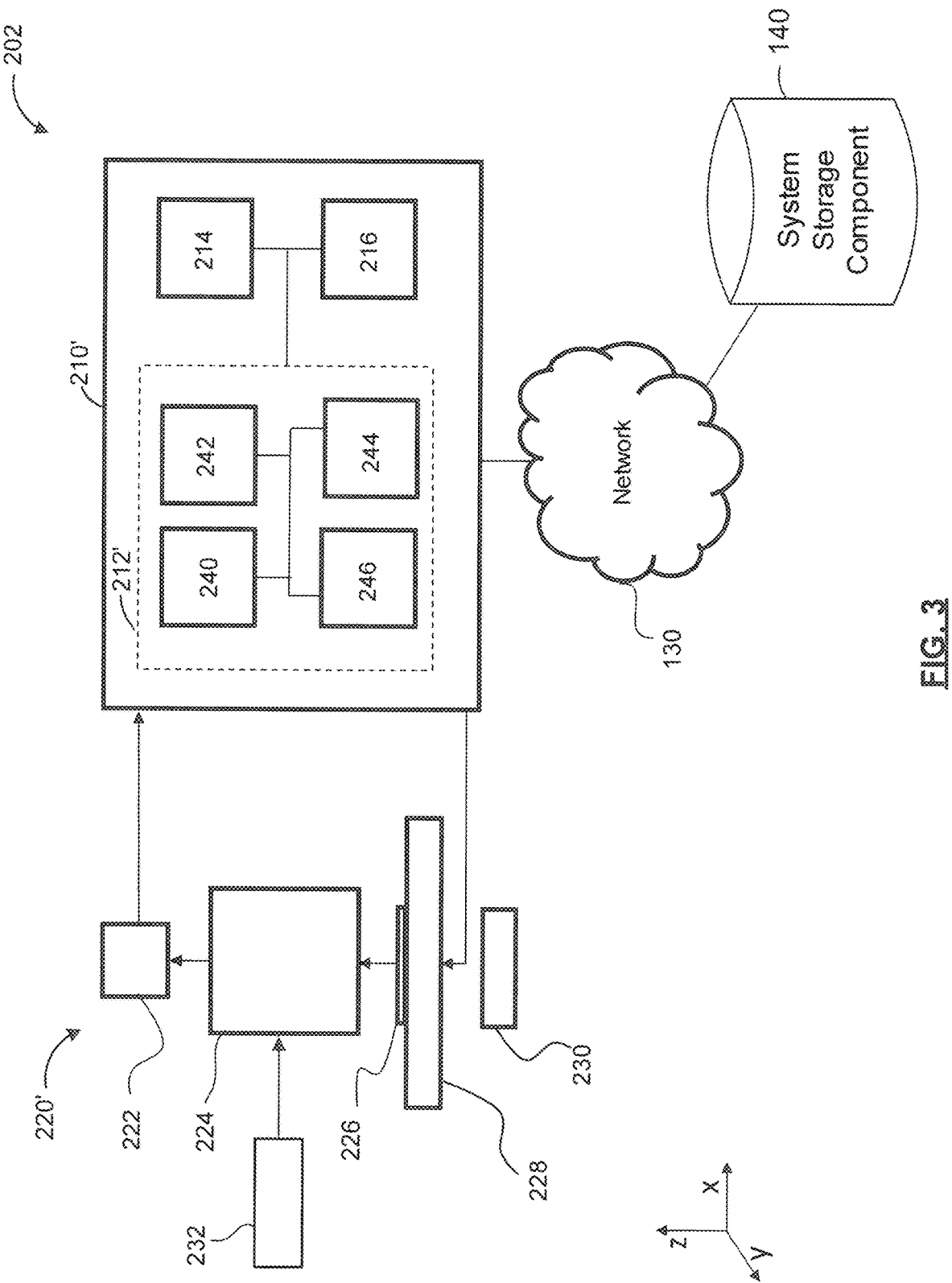
FIG. 3 is a block diagram of another example image management system.

Reference will be made to FIG. 3, which shows a block diagram 202 of an example image management system 210' in communication with an example imaging device 220', and the system storage component 140 via the network 130. For illustrative purposes, in comparison with the block diagram 200 of FIG. 2, the block diagram 202 includes another example imaging device 220' and another example image management system 210'.

The imaging device 220' shown in FIG. 3 includes an epi-illumination component 232 in addition to the bottom illumination component 230 in FIG. 2. The epi-illumination component 232 can enable different types of imaging, such as fluorescence imaging or dark-field imaging. It is understood that the systems and methods described herein are not limited to specific implementations of imaging devices 220, 220'. Imaging devices 220, 220' are shown herein as illustrative examples.

As shown in FIG. 3, the image management system 210' includes the pre-processing component 240, the indexing component 242, the searching component 244, the communication component 216, and the storage component 214. In this example, the image management system 210' includes a reporting component 246. Each of components 240, 242, 244, 246 may also be implemented with hardware or software, or a combination of both. For example, components 240, 242, 244, 246 can include computer programs executable by the processor 212' to conduct the intended operations.

The reporting component 246 can generate a report based on the imaging data received from the imaging device 220'. For example, the reporting component 246 can identify similar reports from the storage component 214 and extract relevant report data from the identified reports for generating the report for the imaging data received from the imaging device 220'. An example report can include data related to various characteristics including, but not limited to, procedure type, specimen focality, tumor site, tumor focality, microscopic features of tumor, histologic type, histologic features, and histologic grade.

Although the reporting component 246 is shown separate from components 240, 242, 244, the reporting component 246, the pre-processing component 240, the indexing component 242, and the searching component 244 can be combined into a fewer number of components or may be separated into further components, in some embodiments. For example, the reporting component 246 and the searching component 244 can be combined. FIG. 4 shows, generally at 204, an example image management system 310 in which the pre-processing component 240, the indexing component 242, the searching component 244, the reporting component 246, and the storage component 214 are provided at a computing device (such as but not limited to smart phone, tablet, etc.). For example, the functionalities of the pre-processing component 240, the indexing component 242, the searching component 244, and/or the reporting component 246, may be provided via an application stored on the computing device and executable by a processor at the computing device. In this example, the searching component 244 and the reporting component 246 are combined together. As described, the computing device 310 can include a mobile computing device, such as a smart phone or tablet, instead of a workstation computer. Although mobile computing devices often have reduced computing power capabilities than workstation computers, a more portable and inexpensive image management system 310 can be provided.

Figure 5A:
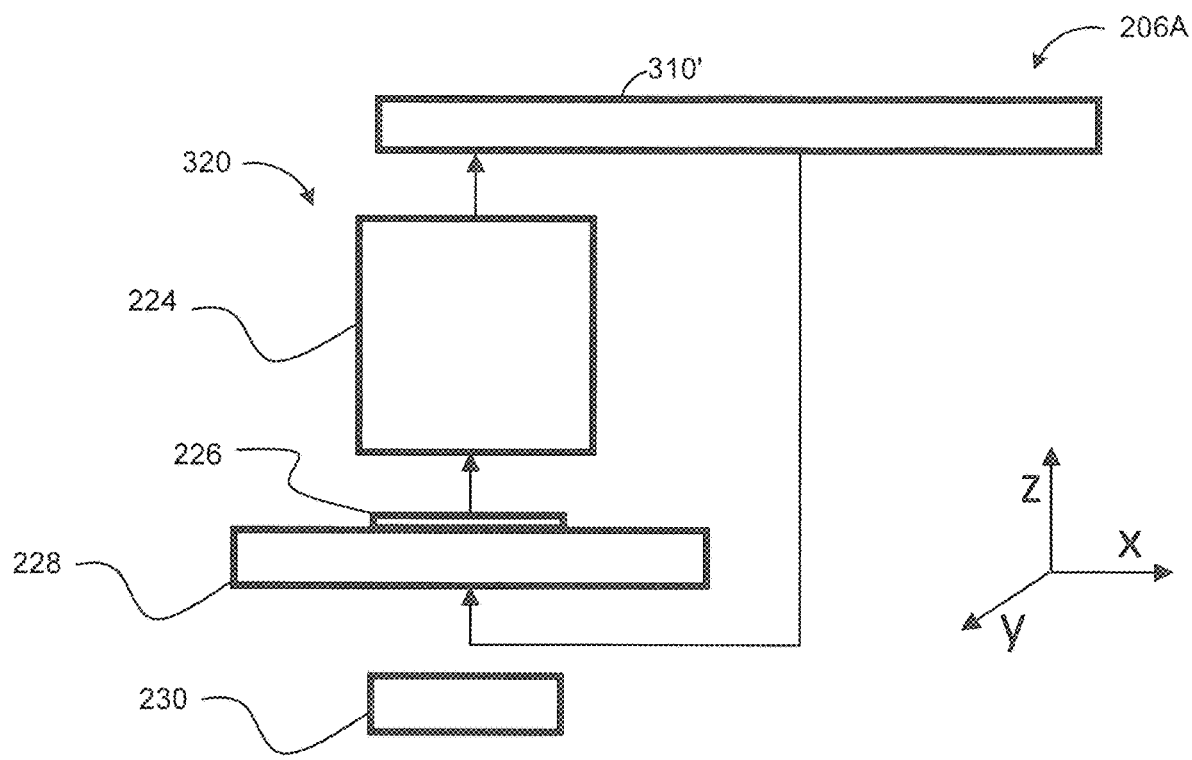
FIG. 5A is a block diagram of another example image management system.

In some embodiments, as shown in FIG. 5A at 206A, an example image management system 310' can be implemented with a mobile computing device with an imaging component so that a simpler external imaging device 320 can be used. For example, the imaging component at the mobile computing device can interface with the external imaging device 320 (e.g., microscope) via an optical adaptor. The mobile computing device can, in some embodiments, be a smart camera adapted to conduct the functionalities of the image management system 310'.

Figure 5B:
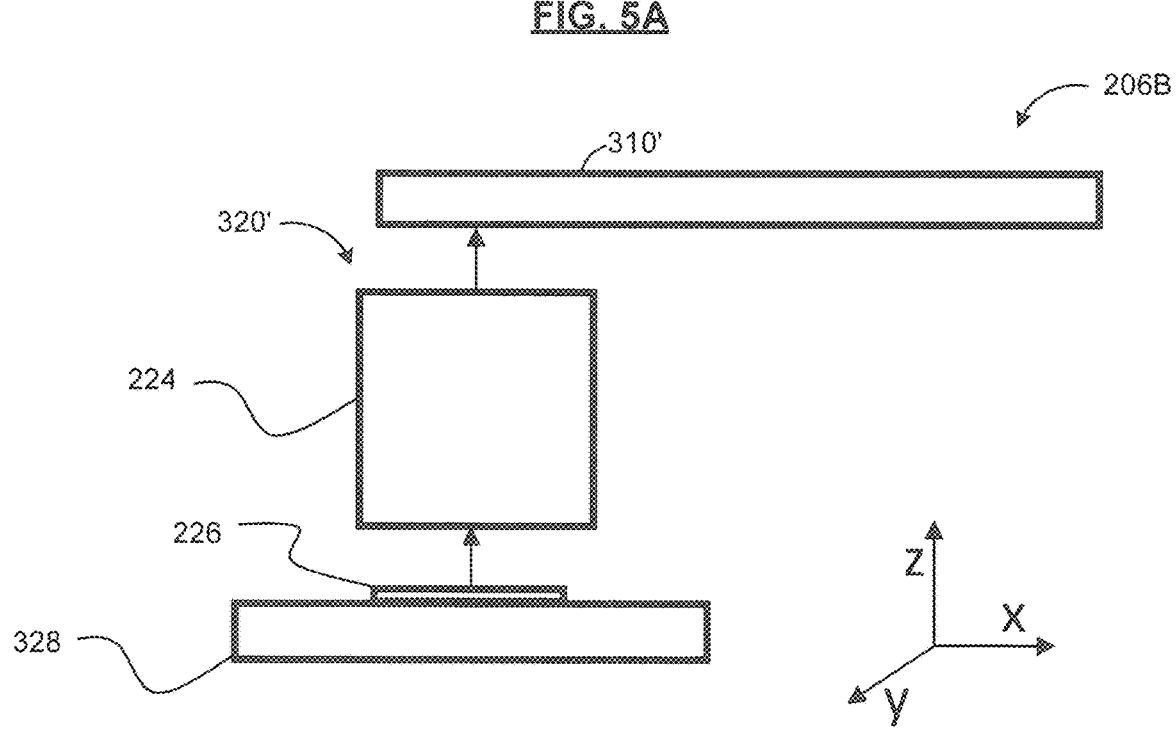
FIG. 5B is a block diagram of the example image management system of FIG. 5A in operation with another example external imaging device.

Although the imaging resolution and speed are reduced with the image management system 310' (in comparison with systems in which an external imaging component 222 is used, such as in FIGS. 2 to 4), the image management system 310' can be provided as a more mobile solution and also at a lower cost. Since the internal imaging component at the mobile computing device 310' is likely to have a lower resolution than the external imaging component 222 in FIGS. 2 to 4, the image management system 310' can be used with a lower resolution positioning stage 228 as well. For example, FIG. 5B shows generally at 206B the example image management system 310' in operation with a simplified external imaging device 320'. The external imaging device 320' does not include a motorized stage and instead, a manual positioning stage 328 with illumination can be provided.

Although not explicitly shown in FIGS. 5A and 5B, the mobile computing device 310' can communicate via the network 130 with the system storage component 140 and/or other computing devices, as required for the operation of the image management system 310'. For example, in remote environments, the mobile computing device 310' can communicate via cellular and/or satellite networks.

Figure 6:
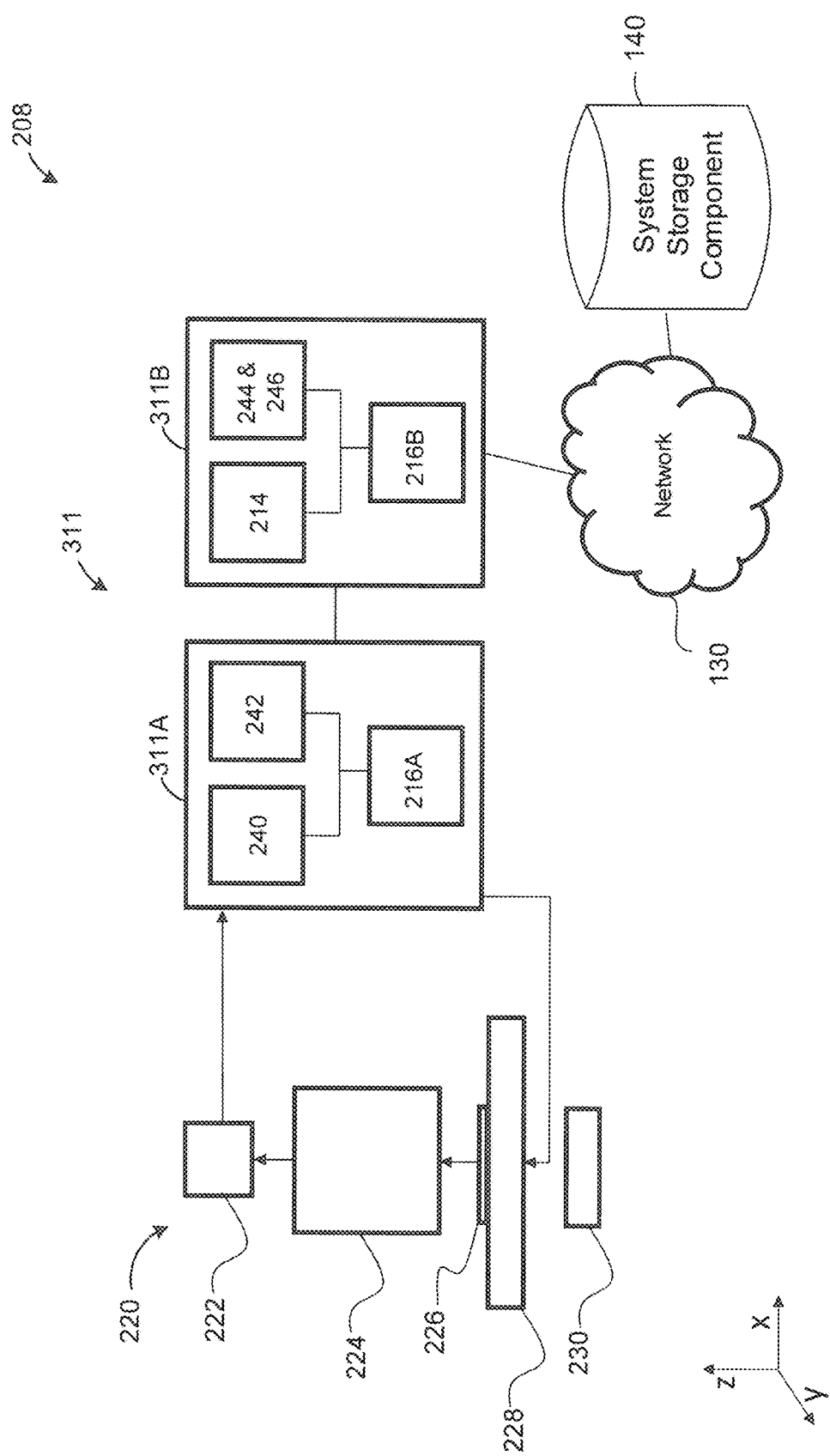
FIG. 6 is a block diagram of another example image management system.

FIG. 6 shows a block diagram 208 of another example image management system 311 in communication with imaging device 220 and the system storage component 140 via the network 130.

The image management system 311 includes a first image management sub-system 311A and a second image management sub-system 311B. The first image management sub-system 311A includes the pre-processing component 240, the indexing component 242, and a first communication component 216A, and the second image management sub-system 311B includes the storage component 214, the searching component 244, the reporting component 246, and a second communication component 216B. Although not shown in FIG. 6, each of the first image management sub-system 311A and the second image management sub-system 311B includes a respective processor operable to conduct the methods and systems described herein.

The first and second image management sub-systems 311A and 311B can be implemented with different computing resources that can be in electronic communication with each other. The first and second image management sub-systems 311A and 311B can communicate with each other via wired and/or wireless communication. The first image management sub-system 311A can act as the interface between the imaging device 220 and the second image management sub-system 311B.

For example, the first and second image management sub-systems 311A and 311B can be provided with different computing devices. Due to the different functionalities of the first and second image management sub-systems 311A and 311B, the computing resources required for each of the first and second image management sub-systems 311A and 311B can vary. For example, since the first image management sub-system 311A includes the pre-processing and indexing components 240, 242, the computing device providing the first image management sub-system 311A requires greater processing resources than the computing device providing the second image management sub-system 311B. It may be possible for the second image management sub-system 311B to be provided via an application at a smart phone, tablet, or a computer with less processing resource. In some embodiments, the first image management sub-system 311A can also be implemented with a computing device with an imaging component, such as a smart phone, tablet and/or a smart camera adapted to perform the functionalities of the first image management sub-system 311A. In remote locations, for example, the first image management sub-system 311A can operate to capture the image(s), pre-process the image(s), generate the indices based on the image(s) and store the indices and image(s) for transmission to the second image management sub-system 311B later on (e.g., when network connectivity becomes available).

Figure 7:
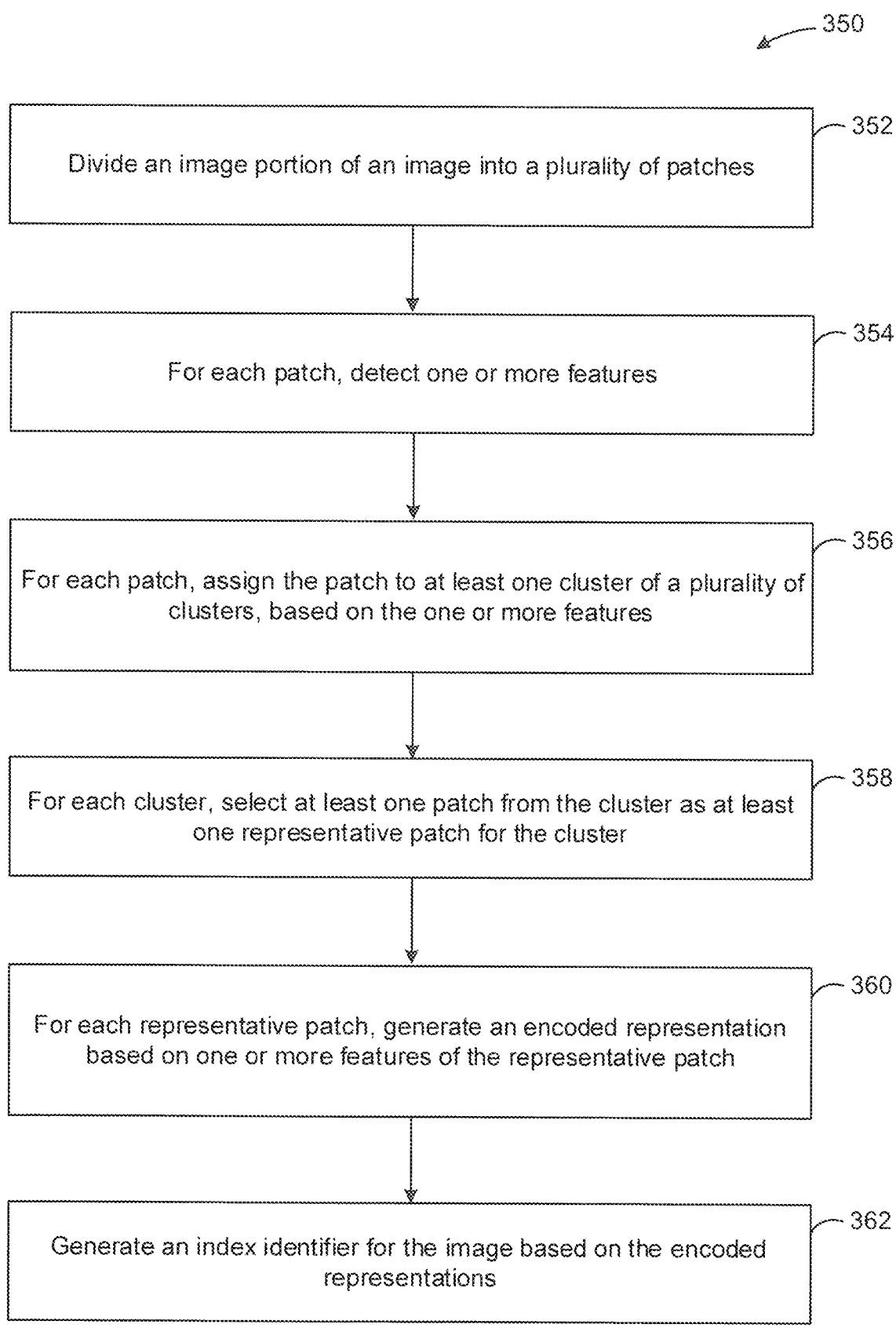
FIG. 7 is a flowchart of an example method for indexing an image, in accordance with an example embodiment.

Referring now to FIG. 7, an example method 350 for indexing an image is shown in a flowchart diagram. To assist with the description of the method 350, reference will be made simultaneously to FIGS. 9A to 15.

In some embodiments, the processor 112 receives the image, such as example image 400 of FIG. 9A, and extracts the selected portion from the image. The image 400 can be received from the imaging device 120, the computing device 150, or the system storage component 140.

The processor 112 can extract the image portion by segmenting a foreground of the image, such as foreground 404 of image 400, from a background 402 of the image, such as background 402, and providing the foreground 404 of the image as the image portion 406. To segment the foreground 404 of the image, the processor 112 can label each pixel of the image as either a foreground pixel or a background pixel, based on the intensity value at of that pixel location. The foreground 404 of image 400 represents a specimen, such as a tissue sample.

In some embodiments, the processor 112 receives a selected portion of the image as the image portion. That is, the processor 112 can receive pre-processed image data. For example, the processor 112 can receive image portion 406 of FIG. 9B which substantially contains the foreground 404 from image 400 of FIG. 9A. The image portion 406 can be received from the imaging device 120, the computing device 150, or the system storage component 140.

At 352, the processor 112 divides the image portion, such as example image portion 406 in FIG. 9B, of the image 400 into a plurality of patches 408. Example patches 408a to 408n are shown in FIG. 9B. Patches can include part of the background 402.

In some embodiments, the patches do not overlap. That is, each patch includes different pixels of the image portion 406. Patch 408a to 408n are example patches that do not overlap. In other embodiments, a patch can overlap with a neighboring patch. That is, a patch can include the same pixels as another patch of the image portion 406.

The patches 408 shown in FIG. 9B are square in shape. It is possible for the patches 408 to have different shapes. For example, a patches can have a shape that is a rectangle, triangle, trapezoid, circle, oval, or any other appropriate closed planar figure. Each patch 408 of an image 400 has substantially the same shape.

In some embodiments, the dimension of each patch is characterized by a substantially similar number of pixels. As shown in FIG. 9B, the plurality of patches 408 includes patches 408a to 404n with substantially the same dimensions, that is, substantially the same number of pixels.

In addition, a dimension of the patches 408 can be varied with the applications of the image management system 110, according to user definitions and/or other factors associated with the encoding of the images. For example, the dimension of patch 408 can be defined according to a type of image analysis to be implemented, subject of the image (i.e., anatomy and/or malignancy), and/or magnification of the image. In some embodiments, a dimension of each patch is predefined. In some embodiments, a dimension of each patch is predefined based on the smallest region to be detected.

At 354, for each patch of the image, the processor 112 detects one or more features of the patch defined at 352. In some embodiments, the one or more features can be based on a structure and/or a color. In some embodiments, the processor 112 uses a shift-invariant feature transform (SIFT), local binary pattern (LBP), encoded local projection (ELP), and/or deep features of an artificial neural network to detect features.

At 356, the processor 112 assigns each patch of the image to at least one cluster of a plurality of clusters of the image, based on the features of the patch detected at 354. FIG. 10 shows an example plurality of clusters 420 that includes four clusters 422, 424, 426, and 428. As shown in FIG. 9, a first cluster 422 includes patches 422a to 422ii having similar structures (indicated by same pattern); a second cluster 424 includes patches 424a to 424i2 having similar structures (indicated by same pattern); a third cluster 426 includes patches 426a to 426i3 having similar structures (indicated by same pattern); and a fourth cluster 428 includes patches 428a to 4284 having similar structures (indicated by same pattern). In some embodiments, k-means can be used to assign patches to clusters.

In some embodiments, the processor 112 assigns each patch to only one cluster, as shown in FIG. 10. In other embodiments, clusters can be hierarchical and the processor 112 can assign each patch to one or more clusters of different hierarchies.

In some embodiments, the plurality of clusters of the image is predefined. In some embodiments, the processor 112 determines a number of the plurality of clusters of the image based on a Self-Organizing Map.

At 358, the processor 112 selects at least one patch from each cluster of the image as a representative patch for the cluster. The representative patches can form a mosaic that represents features of the image. An example mosaic 430 is shown in FIG. 11. Example mosaic 430 includes representative patches 422a and 422e from cluster 422, representative patches 424c and 424e from cluster 424, representative patches 426a and 426c from cluster 426, and representative patches 428b and 428d from cluster 428. As shown in FIG. 11, example mosaic 430 includes two patches from each cluster; that is, a same number of patches from each cluster.

In some embodiments, the processor 112 selects a variable number of representative patches for the clusters. That is, the number of representative patches for one cluster can be unequal to the number of representative patches for another cluster. For example, the processor 112 can select some number of representative patches for a first cluster that is unequal to a number of representative patches selected for a second cluster.

At 360, the processor 112 generates an encoded representation based on one or more features of each representative patch of the mosaic. That is, the processor 112 generates a plurality of encoded representations for the image. An example representative patch 440 is shown in FIG. 12 and an example encoded representation 450 of the representative patch 440 is shown in FIG. 13.

In some embodiments, the processor 112 uses a shift-invariant feature transform (SIFT), local binary pattern (LBP), encoded local projection (ELP), and/or deep features of an artificial neural network to detect features of the representative patches. The artificial neural network can be pre-trained or fine-tuned. Any other appropriate descriptive feature can be used as well. In some embodiments, the encoded representation includes integer values, such as example encoded representation 450 of FIG. 13. That is, the encoded representation can be non-binary.

In some embodiments, the processor 112 uses a minimum-maximum method and/or a thresholding method to convert the non-binary encoded representation to a binary encoded representation. That is, the encoded representation including integer values 450 illustrated in FIG. 13 can be encoded in binary form, as illustrated by binary encoded representation 460 of the representative patch 440 is shown in FIG. 14. In some embodiments, the processor 112 can determine a data variation within each non-binary encoded representation 430 by comparing sequential integer values.

In some embodiments, the processor 112 can encode the non-binary encoded representation 430 in binary form by applying the below Equation (1).

$$b(i) = \begin{cases} 1 & \text{if } p(i+1) > p(i), \\ 0 & \text{otherwise} \end{cases} \quad (1)$$

where p is the encoded representation of size n; and
b is the binary encoding of position i, $\forall i \in \{1, 2, \ldots, n-1\}$.

According to Equation (1), the processor 112 can assign bit "1" when a subsequent integer value of the encoded representation increases and bit "0" when the subsequent integer value of the encoded representation decreases. Other representations of the data variation in the integer values, even outside of binary representations, may be applied. In some embodiments, the processor 112 can instead assign bit "0" to represent an increase in a subsequent integer value and a bit "1" to represent a decrease in the subsequent integer value.

As can be seen in FIG. 13, the difference from a first (left-most) integer value 450a (see e.g., "10") to a second integer value 450b (see e.g., "23") is an increase. This increase is represented by the processor 112 in the binary encoded representation 460 shown in FIG. 14 with the bit "1" 460a. Similarly, the difference from the second integer value 450b to a third integer value 450c (see e.g., "54") is an increase. This increase is represented by the processor 112 in the binary encoded representation 460 shown in FIG. 14 with the bit "1" 460b. As well, the difference from the third integer value 450c to a fourth integer value 450d (see e.g., "112") is an increase. This increase is represented by the processor 112 in the binary encoded representation 460 shown in FIG. 14 with the bit "1" 460c. However, the difference from the fourth integer value 450d to a fifth integer value 450e (see e.g., "98") is a decrease. This decrease is represented by the processor 112 in the binary encoded representation 460 shown in FIG. 14 with the bit "0" 460d.

At 362, the processor 112 generates an index identifier for the image based on the encoded representations of the representative patches of the image. FIG. 15 illustrates an example set of encoded representations 470 generated in 360. As shown in FIG. 15, the set of encoded representations 470 includes four encoded representations 470a, 470b, 470c, and 470d.

In some embodiments, the processor 112 generates an index identifier for the image based on the encoded representations of the representative patches of the image by sorting the set of encoded representations based on the entire encoded representations. An example sorted set of encoded representations 480, generated by sorting the unsorted set 470 based on all bits of the encoded representations 470a, 470b, 470c, and 470d is shown in FIG. 15. To provide the sorted set of encoded representations 480, the encoded representations 470a, 470b, 470c, and 470d of the unsorted set 470 have been reordered. That is, the first encoded representation 480a of the sorted set 480 corresponds to the third encoded representation 470c of the unsorted set 470. The second encoded representation 470b of the unsorted set 470 remains as the seconded encoded representation 480b of the sorted set 480. The third encoded representation 480c of the sorted set 480 corresponds to the fourth encoded representation 470d of the unsorted set 470. The fourth encoded representation 480d of the sorted set 480 corresponds to the first encoded representation 470a of the unsorted set 470. The sorted set 480, that is, the ordered set 480 is provided as the index identifier for the image.

In some embodiments, the processor 112 generates an index identifier for the image based on the encoded representations of the representative patches of the image by sorting a portion of the encoded representation. Example sorted sets of encoded representations 492 and 494, generated by sorting the unsorted set 470 based on a portion of the encoded representation is shown in FIG. 15. Sorted set 492 is generated based on a first portion 496, that is, a first three bits of the encoded representations 470a, 470b, 470c, and 470d. As shown in FIG. 15, the sorted set 492 is same as the sorted set 480.

In contrast, sorted set 494 is generated based on a second portion 498, that is, a last three bits of the encoded representations 470a, 470b, 470c, and 470d. For example, the first encoded representation 494a of the sorted set 494 corresponds to the second encoded representation 470b of the unsorted set 470. The second encoded representation 494b of the sorted set 494 corresponds to the fourth encoded representation 470d of the unsorted set 470. The third encoded representation 494c of the sorted set 494 corresponds to the second encoded representation 470b of the unsorted set 470. The fourth encoded representation 494d of the sorted set 480 corresponds to the third encoded representation 470c of the unsorted set 470. The sorted set 492, 494, or both of the sorted sets 492 and 494 can provided as the index identifier for the image.

By sorting portions of the encoded representation, a plurality of sorted sets can be generated. That is, when encoded representations include m bits, n sorted sets can be obtained by sorting n portions of the encoded representations. When all bits are used for sorting, a search of the index identifier is simply a binary search with logarithmic search time.

Finally, the index identifier for the image can be stored in the storage component 114 or in the system storage component 140. The index identifier can be stored with links to the image and/or report or record associated with the image. In some embodiments, if sufficient storage is available, all features of representative patches detected at 360 can be stored.

Figure 8:
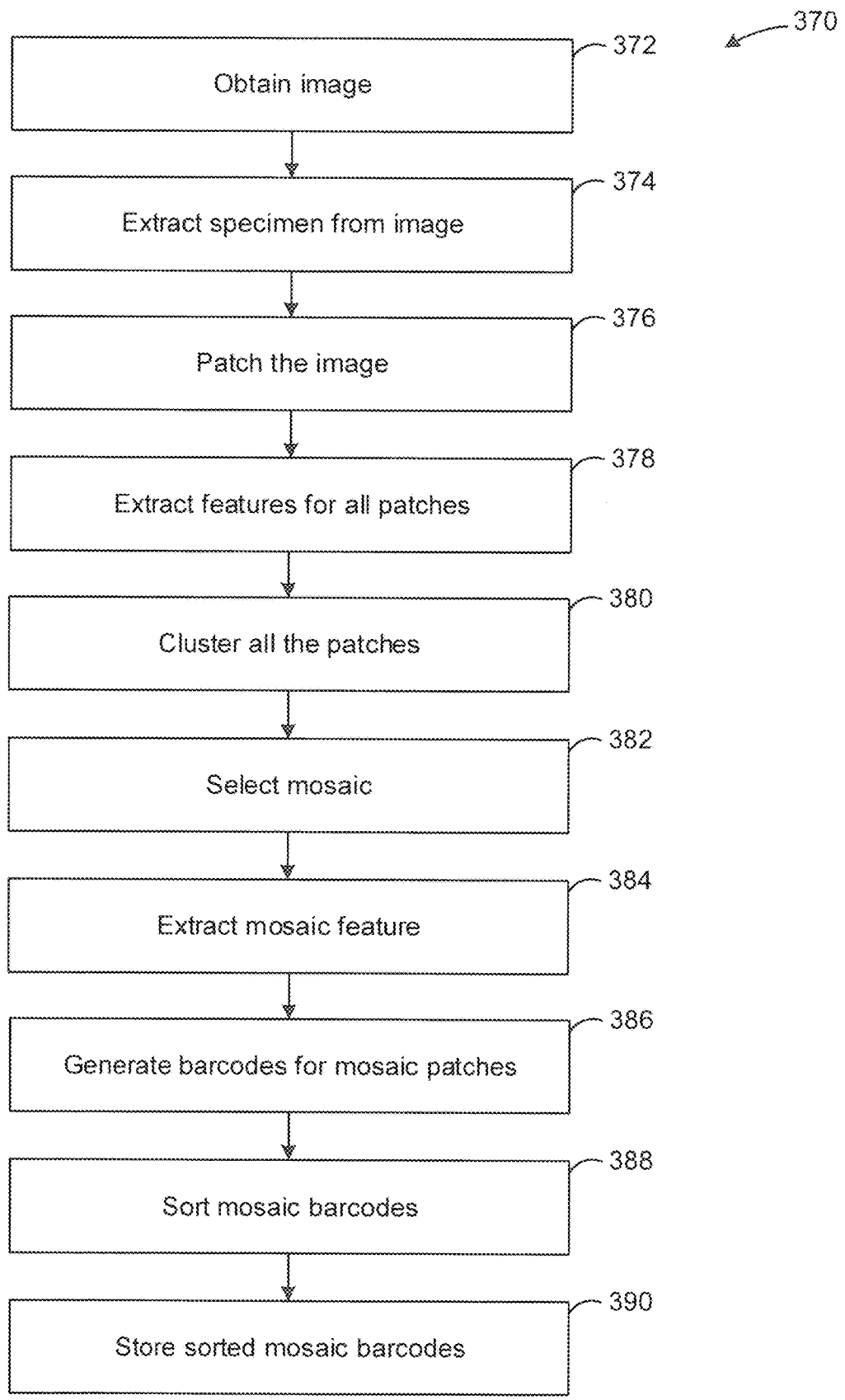
FIG. 8 is a flowchart of another example method for indexing an image.

Reference is now made to FIG. 8, which is a flowchart diagram 370 of another example method for indexing the image 400.

At 372, the processor 112 can obtain the image 400. The image 400 can be obtained from the imaging device 120, the computing device 150, or the system storage component 140.

At 374, the processor 112 can extract a specimen in the foreground 404 of the image 400 by extracting image portion 406 containing the specimen 404 and some of the background 402 as well.

At 376, the processor 112 can patch the image 400. In particular, the processor 112 can divide the image portion 406 extracted at 374 into a plurality of patches 408, similar to 352 of method 350.

At 378, the processor 112 can extract features for all patches 408. That is, the processor 112 can detect features in each patch 408 defined at 376, similar to 354 of method 350.

At 380, the processor 112 can cluster the patches based on the features extracted at 378, similar to 356 of method 350.

At 382, the processor 112 can select a mosaic from the clusters generated at 380. A mosaic can be selected by selecting at least one representative patch from each cluster, similar to 358 of method 350.

At 384, the processor 112 can extract features for all patches of the mosaic.

At 386, the processor 112 can generate barcodes for the mosaic patches based on the features extracted at 384, similar to 360 of method 350.

At 388, the processor 112 can sort the barcodes generated at 386 to generate an index identifier, similar to 362 of method 350.

At 390, the processor 112 can store the barcodes sorted at 388 in the storage component 114 or in the system storage component 140.

Figure 16:
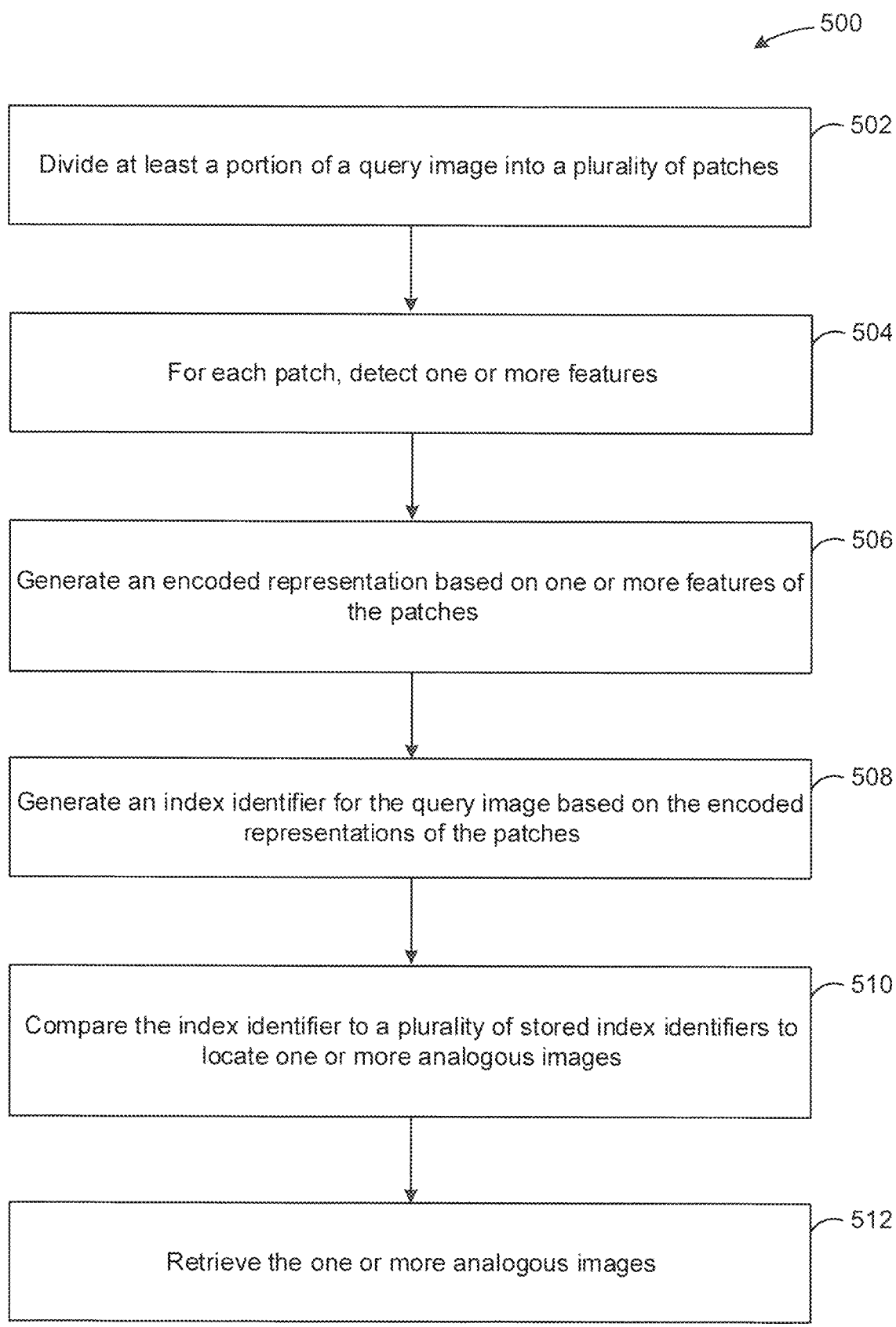
FIG. 16 is a flowchart of an example method of searching for an image, in accordance with an example embodiment.

Reference is now made to FIG. 16, which is a flowchart diagram 500 of an example method of searching for one or more images. A search for one or more images can be performed to retrieve images that are similar to a query image.

In some embodiments, the processor 112 receives a query image.

At 502, the processor 112 divides at least a portion of the query image portion into a plurality of patches, similar to 352 of method 350 and 376 of method 370. The portion of the query image that is divided can relate to a region of interest of an entire query image or to an image portion of the image when the query image is an entire image.

At 504, for each patch of the query image, the processor 112 detects one or more features of the patches defined at 502, similar to 354 of method 350 and 378 of method 370.

At 506, the processor 112 generates an encoded representation based on one or more features of each patch of the query image, similar to 360 of method 350. That is, the processor 112 generates a plurality of encoded representations for the query image.

At 508, the processor 112 generates an index identifier for the query image based on the encoded representations of the patches, similar to 362 of method 350.

At 510, the processor 112 compares the index identifier for the query image with a plurality of stored index identifiers to locate one or more analogous images. The stored index identifiers can be previously generated using the methods 350 or 370.

At 512, the processor 112 retrieves the one or more analogous images. Retrieving the one or more analogous images can involve retrieving one or more reports associated with the one or more analogous images.

Figure 17A:
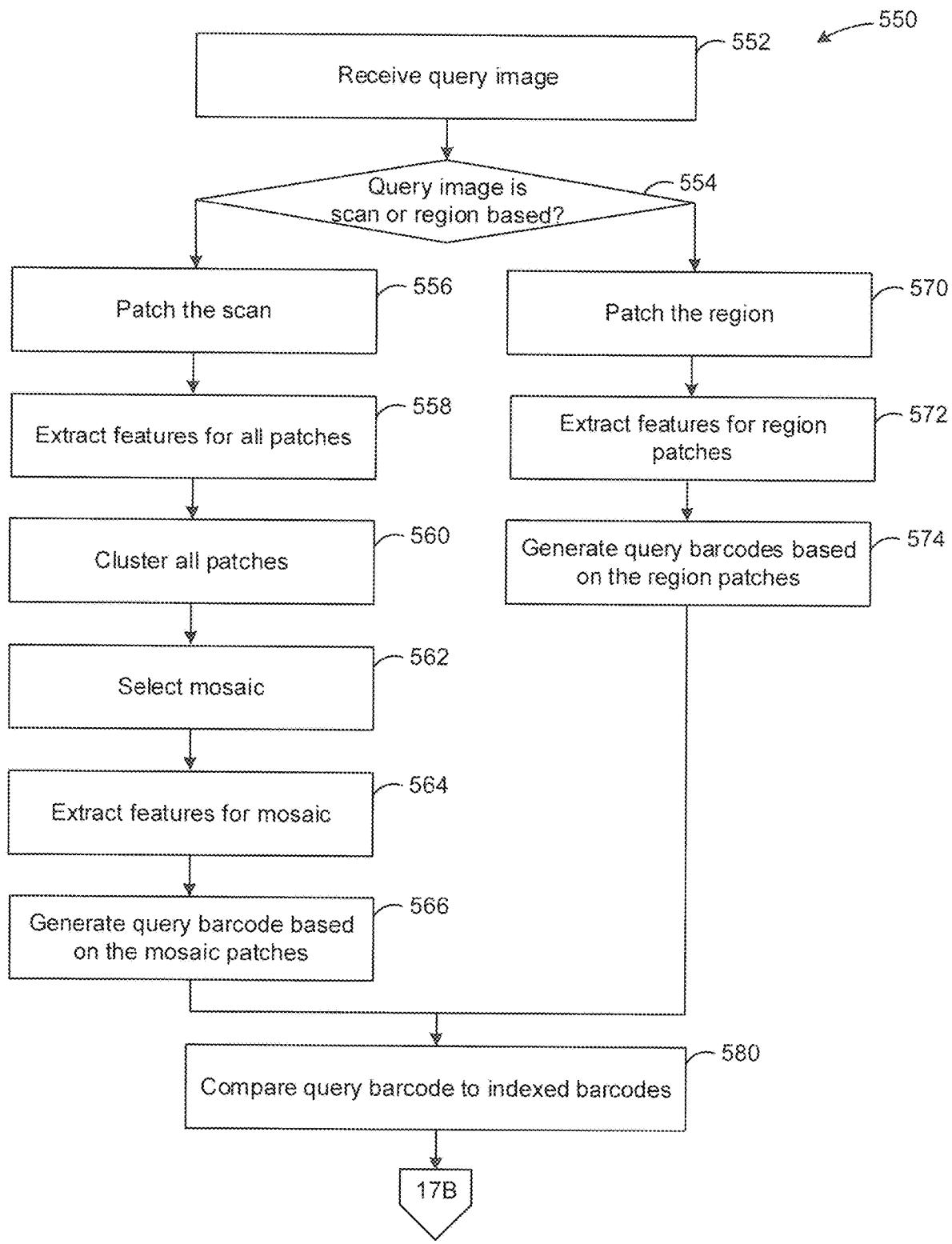
FIGS. 17A and 17B is a flowchart of another example method of searching for one or more images, in accordance with an example embodiment.
Figure 17B:
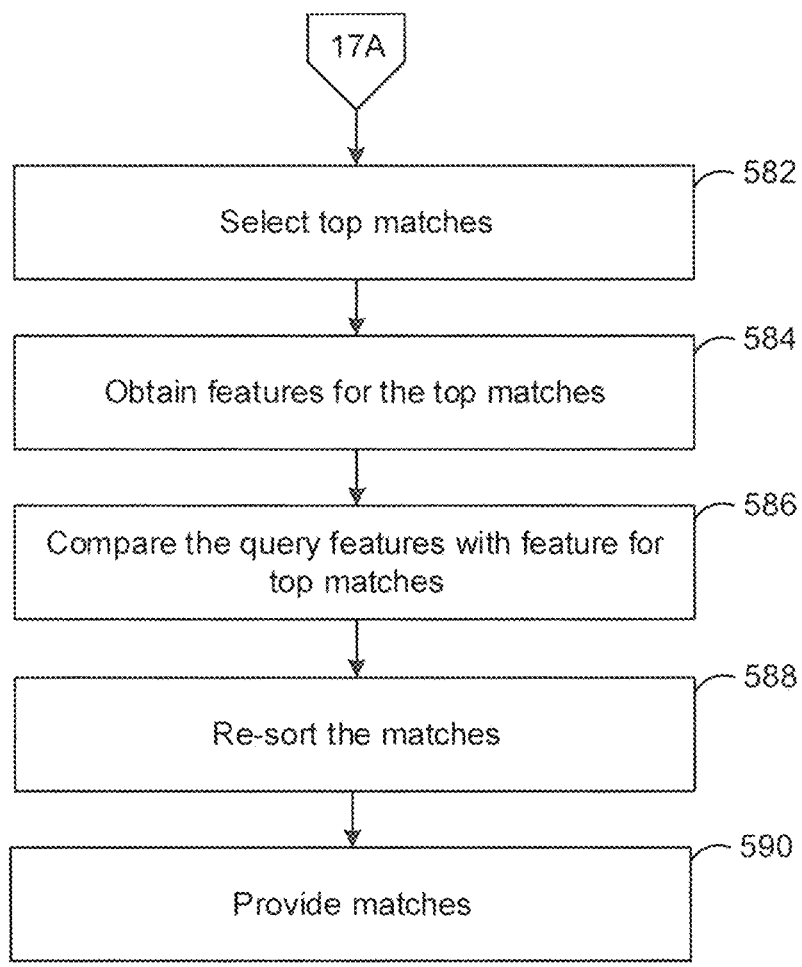

Reference is now made to FIGS. 17A and 17B, which is a flowchart diagram 550 of another example method of searching for one or more images using an index identifier.

At 552, the processor 112 can receive the query image. The query image can be received from the imaging device 120, the computing device 150, or the system storage component 140. The query image can be submitted by a user for examination or analysis of the query image.

At 554, the processor 112 can determine whether the query image received at 552 is a scan based query or a region based query. A scan based query can be directed to an entire query image, that is, the query may not be limited to any specific region of the query image. In contrast, a region based query can be directed to a specific region of interest in the query image.

With a region based query, the query can relate to all patches in the query image or a subset of patches within a selected region of interest in the query image. With a scan based query, the query can relate to the mosaic, that is, the representative patches of the query image.

Any appropriate user selections can be provided at the computing device 150 to select a region of interest in the query image. For example, a user at computing device 150 can select a center of the region of interest or outline the region of interest.

The method 550 can proceed to 556 if the processor 112 determines at 554 that the query is a scan based query. At 556, the processor 112 can patch the scan. That is, the processor 112 can patch the query image, or divide the image into a plurality of patches, similar to 352 of method 350 and 376 of method 370.

At 558, the processor 112 can extract features for all patches of the query image. That is, the processor 112 can detect features in each patch defined at 556, similar to 354 of method 350 and 378 of method 370.

At 560, the processor 112 can cluster the patches based on the features extracted at 558, similar to 356 of method 350 and 380 of method 370.

At 562, the processor 112 can select a mosaic from the clusters generated at 560. A mosaic can be selected by selecting at least one representative patch from each cluster, similar to 358 of method 350 and 382 of method 370.

At 564, the processor 112 can extract features for all patches of the mosaic, similar to 384 of method 370.

At 566, the processor 112 can generate barcodes for the mosaic patches based on the features extracted at 564 to provide a query barcode, similar to 360 of method 350 and 386 of method 370.

If the processor 112 determines at 554 that the query is a region based query, the method 550 can proceed to 570. At 570, the processor 112 can patch the region. That is, the processor 112 can patch a region of interest selected by the user, or divide the region of interest into a plurality of patches (i.e., region patches).

At 572, the processor 112 can extract features for the region patches. That is, the processor 112 can detect features in each region patch defined at 570. In some embodiments, features are extracted from all region patches. In other embodiments, features are extracted from a subset of region patches, depending on a size of the region of interest and/or the variability of image data within the region patches.

At 574, the processor 112 can generate barcodes for the region patches based on the features extracted at 572 to provide a query barcode.

Irrespective of whether the query barcode is generated from the mosaic patches of the query image at 556 to 566 or from the region patches of a region of interest in the query image at 570 to 574, the method 550 proceeds to compare the query barcode to index identifiers of one or more images at 580 stored in the storage component 114 or in the system storage component 140. The comparison of the query barcode with the index identifiers can involve using a Hamming distance and/or other compatible methods, to measure similarity between the query barcode and index identifiers.

At 582, the processor 112 can select the top matches based on the comparison of 580. The top matches can relate to indexed images that are most similar or least dissimilar to the query image. The number of images selected as top matches can be predefined based on the volume of the indexed images and the variation of image data in the indexed images. In order to minimize search time, a very small number of images can be selected as top matches in relation to the total number of indexed images. For scan based searches, the selection of the top matches can relate to the entire mosaic. For region-based searches, the selection of top matches can relate to individual patches.

At 584, the processor 112 can obtain features for the top matches selected at 582. In some embodiments, the features for the top matches are predetermined and stored in the storage component 114 or in the system storage component 140 and obtaining the features at 584 involves retrieving the features from the storage component 114 or in the system storage component 140. If the features for the top matches are not stored in the storage component 114 and in the system storage component 140, obtaining the features at 584 involves extracting features for the top matches, similar to 384 of method 370.

At 586, the processor 112 can compare features of the query image with features of the top matches. In some embodiments, Euclidian, chi-squared method, cosine similarity, and other distance measures can be used for the comparison.

At 588, the processor 112 can re-sort the top matches based on the comparison of 586. In particular, the top matches can be re-sorted in order of descending similarity.

At 590, the processor 112 can provide the re-sorted top matches to a user at the computing device 150. In some embodiments, the re-sorted top matches are displayed in a graphical user interface at computing device 150. Furthermore, in response to a selection received at the computing device 150, a full image of a top match and/or a report associated with a top match can be retrieved and displayed in the graphical user interface at computing device 150.

Indexing one or more images in accordance with the methods and systems described herein can classify the images consistently. The index identifiers can then be organized in data structures to search for and identify analogous images for comparison.

Figure 18:
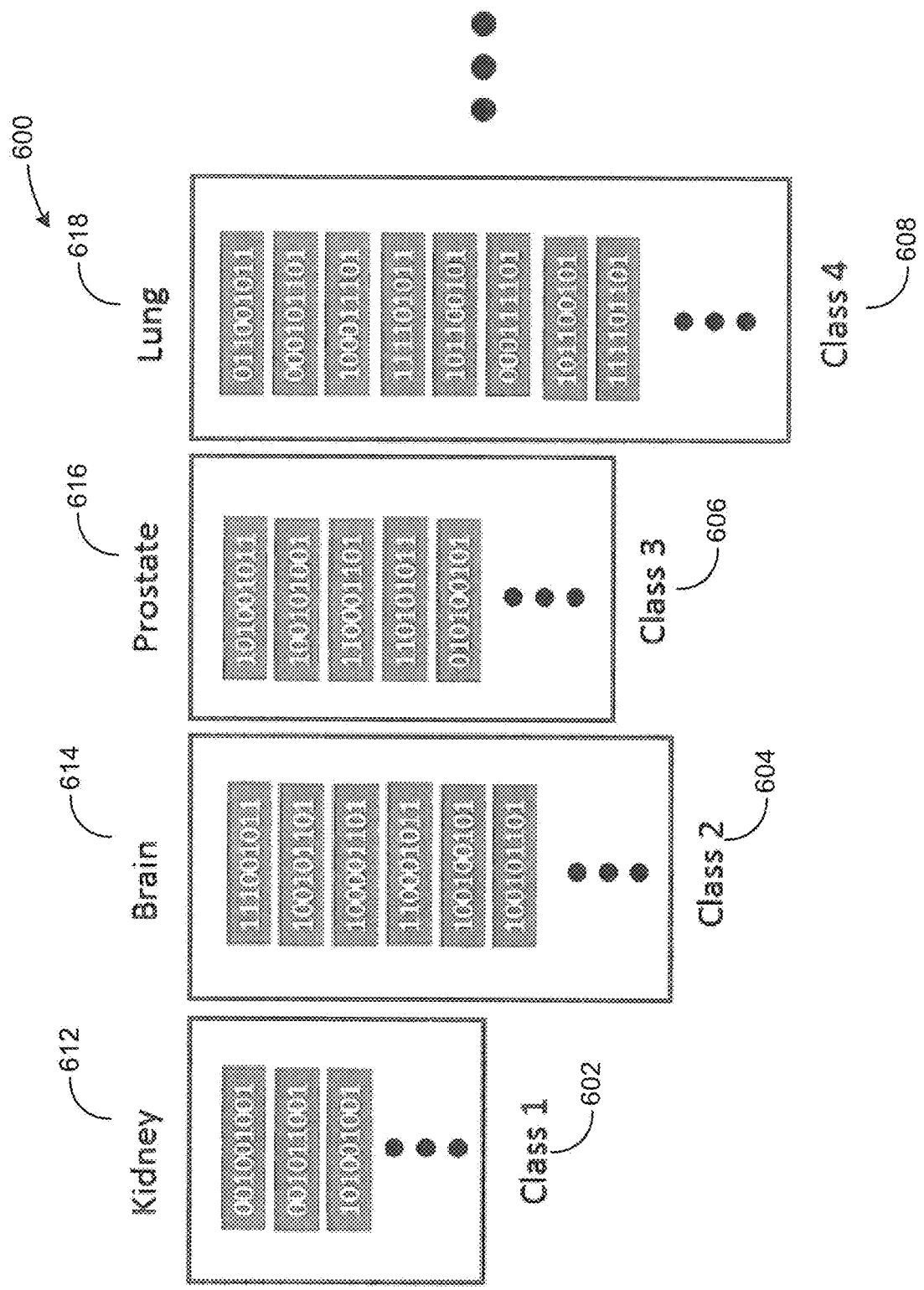
FIG. 18 is a schematic illustrating an example data structure for index identifiers of one or more images.

Reference is now made to FIG. 18, which is a schematic illustrating an example data structure 600 for index identifiers of one or more images. As shown in FIG. 18, the index identifiers are organized in vertical lists for different classes 602, 604, 606, 608. While four classes are shown in data structure 600, data structures can have less or more classes. In the example data structure 600, the classes relate to specific anatomies such as kidney 612, brain 614, prostate 616, and lung 618.

In some embodiments, a search across all classes (herein referred to as a "horizontal search") can identify analogous images containing a similar pattern in another class. For example, a search to identify a pattern representative of cancer in other parts of the body (i.e., in other classes) can help identify an origin of a malignancy. Based on the type, cancer can appear in unexpected organs of the body— prostate cancer may spread to the bones, and lung cancer may spread to the liver. To investigate the origin of a malignancy, a user can select a suspicious tissue region as a region of interest of a query image and submit a horizontal search query. Upon receiving the search query, the processor 112 can search the indexed images by matching the barcode of the query image or the barcode of the region of interest of the query image with all index identifiers of all classes. Hence, given that the volume of indexed images is sufficiently large to provide a diversity of cases, the origin of cancer may be detected by locating a similar pattern in another part of the body (i.e., another class).

In some embodiments, a search within a class (herein referred to as a "vertical search") can identify analogous images containing a similar pattern within the same class. For example, a search to identify a diagnosed case containing a similar pattern in the same part of the body (i.e., same class). In some cases, a user may not be able to confidently diagnose an abnormality. The user can seek peer review, assistance, consultation, confirmation, or verification from another colleague to diagnose the abnormality.

The index identifiers can also be used to search for and identify artifacts within images. Artifacts can negatively affect diagnostic pathology. Carry-over artifacts (i.e., tissue floaters) are a common problem in pathology laboratories. Tissue floaters are generally small pieces of tissue that can be carried over from one tissue sample to another during slide preparation. Some cases can be relatively easily recognized, but in other cases the origin of the suspected tissue floater must be clarified, particularly if the suspected tissue floater contains malignant cells and the remainder of the tissue is benign. Determining the origin of a suspected tissue floater can involve many additional steps. In some cases, the pathologist may need to review all samples of recent days, which is a time-consuming and expensive task. Furthermore, the presence of a suspected tissue floater can lead to a DNA tests or re-biopsies.

Figure 19:
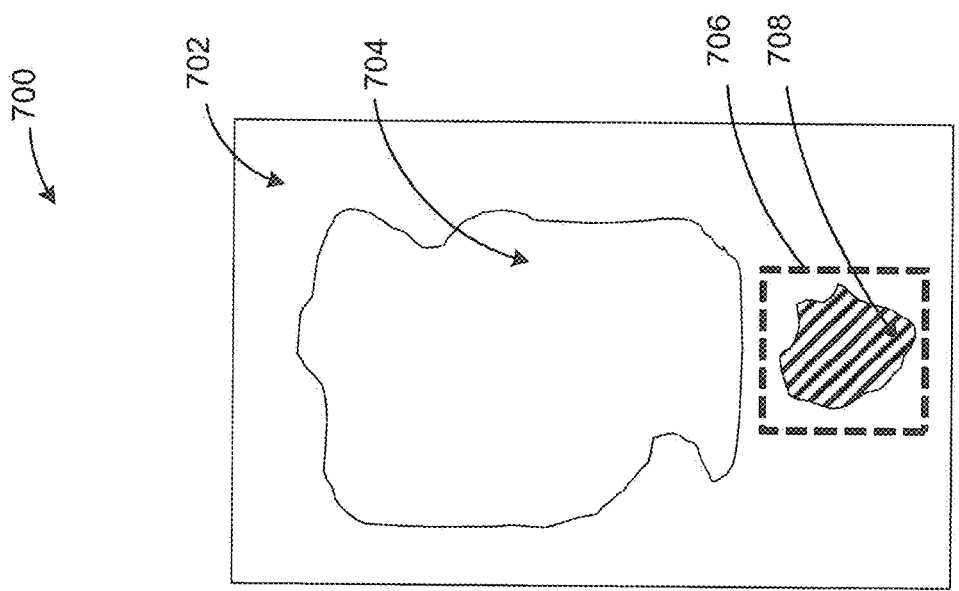
FIG. 19 is a schematic illustrating an example image.

Reference is now made to FIG. 19, which is a schematic illustrating an example image 700. As shown in FIG. 19, image 700 includes a background 702, a specimen 704, as well as a suspected tissue floater 708. In some embodiments, a user can select the suspected tissue floater 708 by outlining 706 the suspected tissue floater 708. In other embodiments, the processor 112 can automatically detect the suspected tissue floater 708 and generate the outline 706 containing the suspected tissue floater 708.

Figure 21:
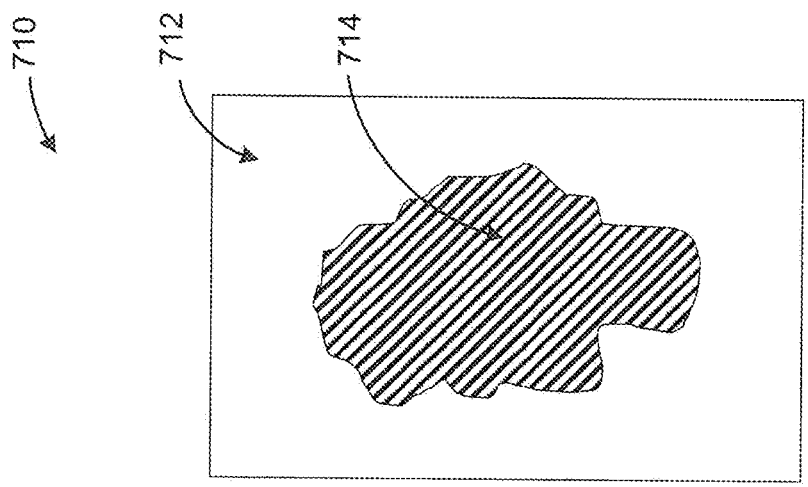
FIG. 21 is a schematic illustrating an example query result.
Figure 20:
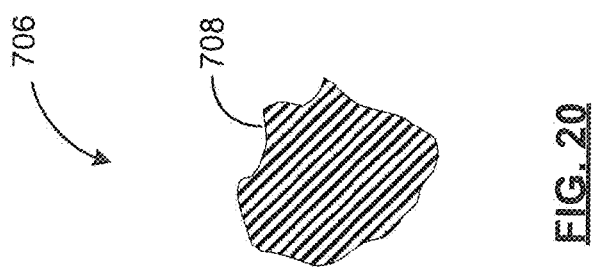
FIG. 20 is a schematic illustrating an example image portion of the image of FIG. 19.

As shown in FIG. 20, the outline 706 extracts the suspected tissue floater 708. The processor 112 can generate one or more query barcodes for the region encompassed by outline 706 and submit the query barcodes for a search for analogous images in neighbouring images containing a similar pattern as the suspected tissue floater 708. That is, the search is limited to images captured in relatively recent to the image 700, or in proximity to image 700. An example image 710 containing a similar pattern as the suspected tissue floater 708 is shown in FIG. 21. Example image 710 contains a specimen having a similar pattern as the suspected tissue floater 708 and the suspected tissue floater 708 is clarified as being a tissue floater.

Figure 22:
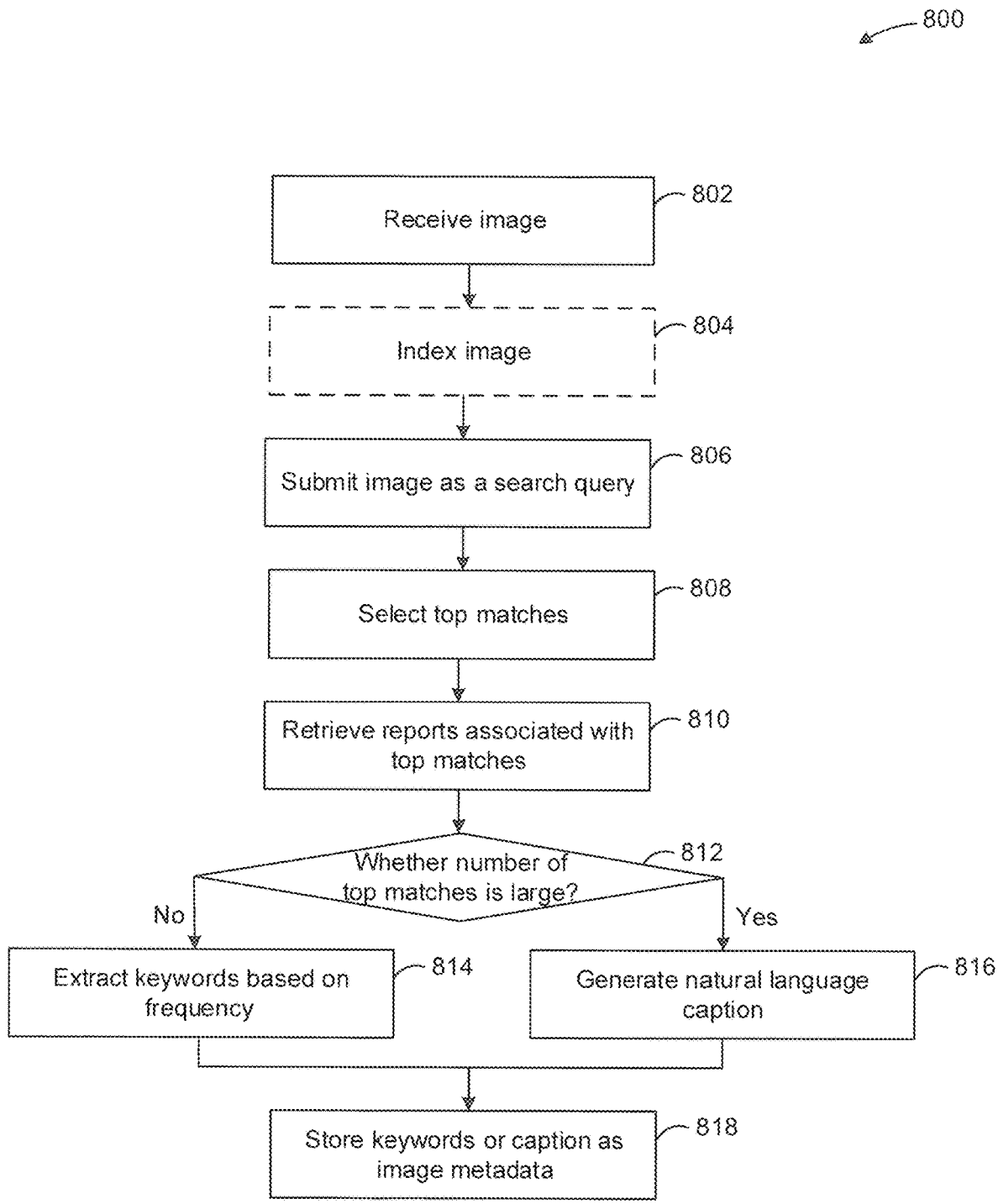
FIG. 22 is a flowchart of an example method for generating caption data for an image, in accordance with an example embodiment.

The index identifiers can also be used to generate caption data for undiagnosed images. Reference is now made to FIG. 22, which is a flowchart of an example method 800 for generating caption data for one or more images. The method 800 can be automatically invoked by the imaging device 120 during or after capture of the image. The method 800 can also be used to caption existing indexed, or unindexed images.

At 802, the processor 112 can receive an undiagnosed image. The undiagnosed image can be received from the imaging device 120, the computing device 150, or the system storage component 140. The undiagnosed image can be submitted by a user for examination or analysis of the undiagnosed image.

At 804, the processor 112 can generate an index identifier for the image, similar to any one of methods 350 of FIG. 7 and 370 of FIG. 8.

At 806, the processor 112 can submit the index identifier generated at 804 for the image as a search query, similar to 580 of method 550 in FIGS. 17A and 17B.

At 808, the processor 112 can select the top matches, similar to 590 of method 550 in FIGS. 17A and 17B.

At 810, the processor 112 can retrieve reports associated with images for the top matches stored in the storage component 114 or in the system storage component 140.

At 812, the processor 112 can determine whether the number of top matches is too large.

If the number of top matches is not large, the method can proceed to 814. At 814, the processor 112 can generate caption data based on the frequency of keywords in the reports retrieved at 810.

If the number of top matches is large, the method can proceed to 816. At 816, the processor 112 can generate caption data based on natural language detected in the reports retrieved at 810. The processor 112 can use recurrent neural networks, such as Long Short Term Memory (LSTM), to detect the natural language in the reports that is meaningful.

At 814, the processor 112 can store the caption data generated at 814 or 816 in the storage component 114 or the system storage component 140. In some embodiments, the caption data can be stored as image metadata.

Figure 23:
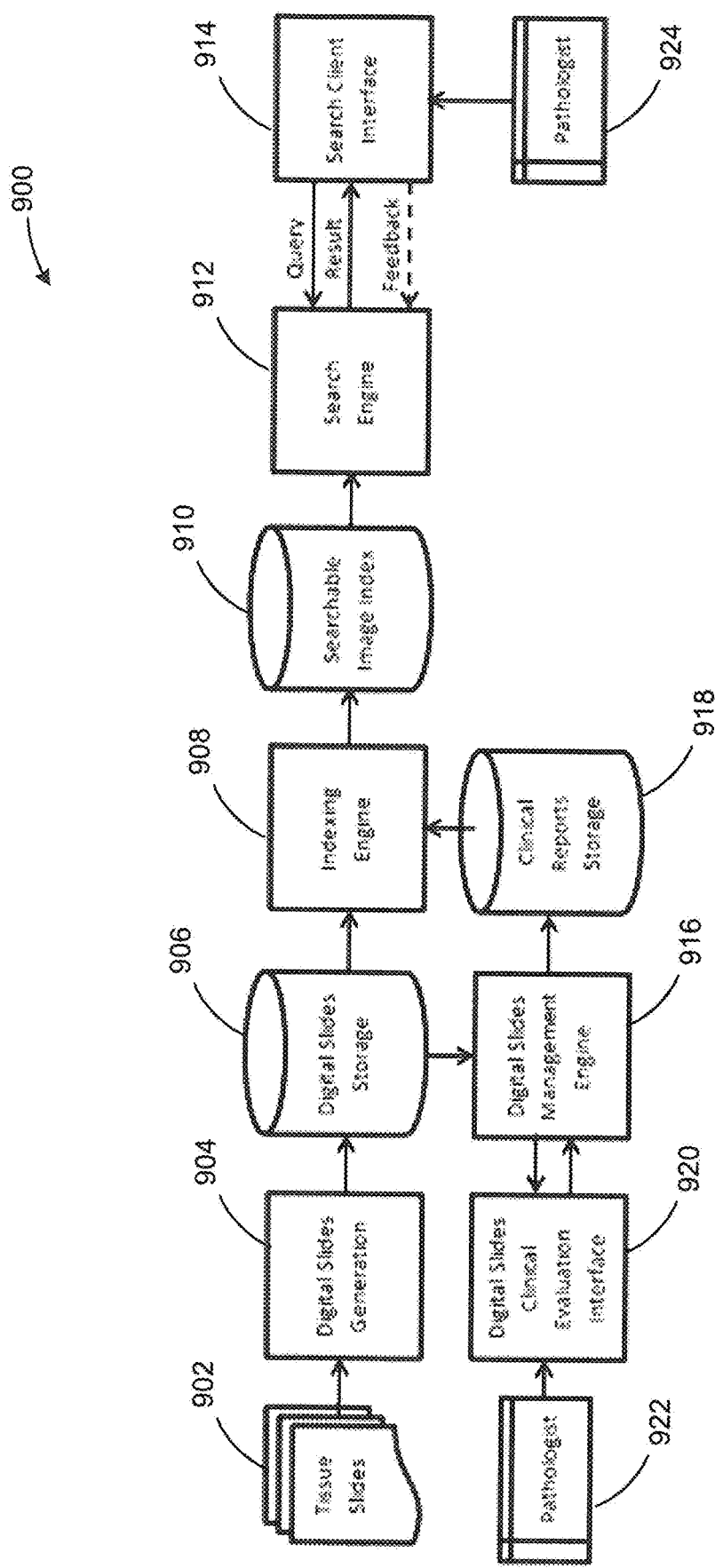
FIG. 23 is a block diagram of a workflow of an imaging system, in accordance with another example embodiment.

Reference is now made to FIG. 23, which illustrates an example block diagram 900 of a workflow of an imaging system. The imaging system includes one or more imaging devices (not shown) for digital slide generation 904, one or more processors (not shown) to provide an indexing engine 908, a search engine 912, and a digital slides management engine 916, one or more storage components (not shown) to provide digital slide storage 906, a searchable image index 910, and clinical reports storage 918, and one or more computing devices (not shown) to provide a search client interface 914 and a digital slides clinical evaluation interface 920. In some embodiments, the digital slide generation 904, indexing engine 908, and search engine 912 can be provided by one processor. In some embodiments, the digital slides storage 906 and the searchable image index 910 can be provided by one storage component (not shown).

The one or more imaging devices can be similar to imaging device 120 of FIG. 1. The one or more processors can be similar to the processor 112 of FIG. 1. The one or more storage components can be similar to the storage component 114 or the system storage component 140 of FIG. 1. The one or more computing devices can be similar to the computing device 150 of FIG. 1.

Furthermore, the one or more imaging devices, one or more processors, one or more storage components, and one or more computing devices can be in communication via a network (not shown), similar to network 130 of FIG. 1. The network provides sufficient bandwidth between any two modules in the workflow that interact together to achieve the depicted workflow.

The one or more imaging devices are instruments that can handle glass tissue slides 902 and generating digital slides 904 that are fully equivalent to the corresponding glass tissue slides 902 under the microscope. The one or more imaging devices can also store the digital slides in a digital slides storage 906. In some embodiments, the one or more imaging devices are slide scanners that have integrated capabilities of indexing output images automatically—that is, so that images are immediately indexed upon acquisition. Furthermore, in some embodiments, the one or more imaging devices can also expose a search engine 912 to clients to execute their search queries.

The digital slides storage 906 is a storage medium that can store multiple digital slides. The digital slides storage 906 allows for the retrieval of the slides for viewing, image processing, and/or machine learning tasks.

The indexing engine 908 can access the digital slides storage 906 and index one or more single slides stored in the digital slides storage 906, in accordance with the methods and systems described herein. The features along with links to the associated digital slide in the digital slides storage 906 and links to associated clinical reports in the clinical reports storage 918 can be stored in the searchable image index 910.

The searchable image index 910 contains searchable records of digital slides. Each digital slide record can hold at least one of the following data: the searchable identifying features of the slide, a link to the digital slide image on the digital slides storage 906, and a link to the clinical reports associated with the slide on the clinical reports storage 918.

The search engine 912 can be serving one or more search client interface(s) 914 simultaneously, if required. A query from a search client interface 914 can include a region of interest from a digital slide. Once a query is received by the search engine 912, the search engine 912 extracts identifying features of the region of interest and compares it against the features available in the searchable image index 910. The search engine 912 then returns a result that includes similar digital slides and regions of interest(s) upon which that similarity was established within the returned digital slides. The result can also include links to view the similar slides on the digital slides storage 906 and to their associated clinical reports on the clinical reports storage 918. The extent of clinical data returned and whether patient identification is shared can depend on the authentication and clearance level of a client at search client interface 914, such as the pathologist 924. Furthermore, the pathologist 924 via the search client interface 914 can provide feedback regarding the quality of the results returned. The search engine 912 can use this feedback to evolve and increase its search accuracy.

The search client interface 914 is a client application that can connect to the search engine 912 and request digital slide search results. The search client interface 914 allows a client, such as pathologist 924, with valid credentials to access a digital slide image and submit a query composed of a region of interest on the digital slide. The search client interface 914 can also receive, display and browse the search results and associated clinical data.

The digital slides clinical evaluation interface 920 is a client application that can connect to the digital slides management engine 912 and retrieve digital slides from the digital slides storage 906. It allows a client, such as a pathologist 922, with valid credentials to access clinical reports in the clinical reports storage 918, including creating clinical reports and adding annotations to the digital slides to emphasize key areas of interest.

The digital slides management engine 916 serve images on the digital slides storage 906 to pathologists 922 connected via the clinical evaluation interface 920. The engine enforces the security of the digital slides data by authenticating the client connected and based on the client identity serve only the slides/cases the client is authorized to access. Furthermore, the digital slides management engine 916 can be responsible for capturing the diagnostic reports and annotations and storing them securely on the clinical reports storage 918.

The clinical reports storage 918 is a storage medium that can store clinical reports associated with digital slides or cases. The clinical reports storage 918 allows for the retrieval of the data for permitted clients and services. Furthermore, the retrieved data can be anonymized, partially anonymized/identified, or fully identified depending on the application/service and the identity of retriever 922, 924 at the search client interface 914 or the digital slides clinical evaluation interface 920.

In some embodiments, the search client interface 914 and the digital slides clinical evaluation interface 920 can be integrated in a single client interface to allow a user to access slides within undiagnosed cases and retrieve search results that aid their decision making process regarding the new undiagnosed cases. Such an integrated platform can become the main dashboard through which users access cases, utilize searches, and create final clinical reports.

In some embodiments, multiple imaging devices can be used with a single search engine 912. For example, a clinical site can use multiple scanners or have a large number of search client interfaces 914. In such cases, the imaging devices can provide both the digital slide generation 904 and the indexing engine 908. A processor can access a combined searchable image index 910 and provide the search engine 912 function to the search client interfaces 914.

In some embodiments, multiple imaging devices can be used in conjunction with a central processor providing both the indexing engine 908 and the search engine 912. The indexing and search related functions are offloaded from the imaging devices and on the processor. Each imaging device is responsible for digital slide generation 904 only.

It will be appreciated that numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that the term "coupled" used herein indicates that two elements can be directly coupled to one another or coupled to one another through one or more intermediate elements.

The embodiments of the systems and methods described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example and without limitation, the programmable computers (referred to below as computing devices) may be a server, network appliance, embedded device, computer expansion module, a personal computer, laptop, personal data assistant, cellular telephone, smart-phone device, tablet computer, a wireless device or any other computing device capable of being configured to carry out the methods described herein.

In some embodiments, the communication interface may be a network communication interface. In embodiments in which elements are combined, the communication interface may be a software communication interface, such as those for inter-process communication (IPC). In still other embodiments, there may be a combination of communication interfaces implemented as hardware, software, and combination thereof.

Program code may be applied to input data to perform the functions described herein and to generate output information. The output information is applied to one or more output devices, in known fashion.

Each program may be implemented in a high level procedural or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g. ROM, magnetic disk, optical disc) readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

Various embodiments have been described herein by way of example only. Various modification and variations may be made to these example embodiments without departing from the spirit and scope of the invention, which is limited only by the appended claims. Also, in the various user interfaces illustrated in the drawings, it will be understood that the illustrated user interface text and controls are provided as examples only and are not meant to be limiting. Other suitable user interface elements may be possible.

We claim:

1. A computer-implemented method of encoding one or more medical whole slide query images for searching, the method comprising:
operating a device processor to:
for each medical whole slide query image,
divide the medical whole slide query image into a plurality of image portions, each image portion comprising at least a specimen portion of a specimen being examined on that medical whole slide query image;
for each image portion, detect one or more features within the associated specimen portion and assign that image portion to one or more feature groups based on the detected one or more features;
from each feature group, select at least one image portion as a representative image portion for that feature group;
generate an encoded representation based on the representative image portion of each feature group, wherein the encoded representation is generated based on one or more features of the representative image portion, and wherein an unselected image portion of at least one feature group comprises an image portion not selected as the representative image portion for the at least one feature group, the unselected image portion comprises a non-feature portion of the specimen portion, the encoded representation does not include the non-feature portion of the unselected image portion; and
generate an index identifier for that medical whole slide query image based on one or more encoded representations generated for the one or more feature groups; and
operating a management processor remote from the device processor to:
receive the index identifier from the device processor;
compare the index identifier with a plurality of stored index identifiers to locate one or more analogous images; and
retrieve the one or more analogous images.

2. The method of claim 1, wherein generating the encoded representation further comprises using at least one of a minimum-maximum method and a thresholding method to convert a non-binary encoded representation to a binary encoded representation.

3. The method of claim 1, wherein comparing the index identifier with the plurality of stored index identifiers to locate the one or more analogous images comprises determining a measure of similarity between the index identifier and each index identifier of the plurality of stored index identifiers.

4. The method of claim 3, wherein determining the measure of similarity between the index identifier and each of the plurality of stored index identifiers comprises determining a Hamming distance between the index identifier and each of the plurality of stored index identifiers.

5. The method of claim 1 comprises operating the device processor to pre-process each medical whole slide query image prior to dividing the medical whole slide query image into a plurality of image portions.

6. The method of claim 1, wherein retrieving the one or more analogous images comprises retrieving a predefined number of images having highest measures of similarity.

7. The method of claim 1, wherein retrieving the one or more analogous images comprises retrieving the one or more analogous images having a measure of similarity greater than a predefined threshold.

8. The method of claim 1 comprises:
for each analogous image:
detecting one or more features of the analogous image;
determining a measure of similarity between the one or more features of the analogous images and the one or more features of each respective medical whole slide query image; and
sorting the one or more analogous images based on the measure of similarity between each of the one or more features of the analogous images and the one or more features of each respective medical whole slide query image.

9. The method of claim 8, wherein the measure of similarity comprises at least one of a Euclidean distance, chi-square distance, and cosine similarity.

10. The method of claim 1 further comprises automatically generating a report for the medical whole slide query image based on the retrieved one or more analogous images.

11. The method of claim 10 comprises operating the device processor to transmit the index identifier to the management processor via a network.

12. A system for encoding one or more medical whole slide query images for searching, the system comprising:
a device processor operable to:
for each medical whole slide query image,
divide the medical whole slide query image into a plurality of image portions, each image portion comprising at least a specimen portion of a specimen being examined on that medical whole slide query image;
for each image portion, detect one or more features within the associated specimen portion and assign that image portion to one or more feature groups based on the detected one or more features;
from each feature group, select at least one image portion as a representative image portion for that feature group:
generate an encoded representation based on the representative image portion of each feature group, wherein the encoded representation is generated based on one or more features of the representative image portion, and wherein an unselected image portion of at least one feature group comprises an image portion not selected as the representative image portion for the at least one feature group, the unselected image portion comprises a non-feature portion of the specimen portion, the encoded representation does not include the non-feature portion of the unselected image portion; and
generate an index identifier for that medical whole slide query image based on one or more encoded representations generated for the one or more feature groups; and
a management processor remote from the device processor, the management processor operable to:
receive the index identifier from the device processor;
compare the index identifier with a plurality of stored index identifiers to locate one or more analogous images; and
retrieve the one or more analogous images.

13. The system of claim 12, wherein the device processor is operable to use at least one of a minimum-maximum method and a thresholding method to convert a non-binary encoded representation to a binary encoded representation.

14. The system of claim 12, wherein the management processor is operable to determine a measure of similarity between the index identifier and each index identifier of the plurality of stored index identifiers.

15. The system of claim 14, wherein the management processor is operable to determine a Hamming distance between the index identifier and each of the plurality of stored index identifiers as the measure of similarity.

16. The system of claim 12, wherein the device processor is operable to pre-process each medical whole slide query image prior to dividing the medical whole slide query image into a plurality of image portions.

17. The system of claim 12, wherein the management processor is operable to retrieve a predefined number of images having highest measures of similarity as the one or more analogous images.

18. The system of claim 12, wherein the management processor is operable to retrieve the one or more analogous images having a measure of similarity greater than a predefined threshold.

19. The system of claim 12, wherein the management processor is operable to:
for each analogous image:
detect one or more features of the analogous image;
determine a measure of similarity between the one or more features of the analogous images and the one or more features of each respective medical whole slide query image; and
sort the one or more analogous images based on the measure of similarity between each of the one or more features of the analogous images and the one or more features of each respective medical whole slide query image.

20. The system of claim 19, wherein the measure of similarity comprises at least one of a Euclidean distance, chi-square distance, and cosine similarity.

21. The system of claim 12, wherein the management processor is operable to automatically generate a report for the medical whole slide query image based on the retrieved one or more analogous images.

22. The system of claim 21, wherein the device processor is operable to transmit the index identifier to the management processor via a network.

* * * * *

UNITED STATES PATENT AND TRADEMARK OFFICE
CERTIFICATE OF CORRECTION

PATENT NO. : 11,769,582 B2  
APPLICATION NO. : 16/674508  
DATED : September 26, 2023  
INVENTOR(S) : Hamid Reza Tizhoosh et al.

It is certified that error appears in the above-identified patent and that said Letters Patent is hereby corrected as shown below:

In the Specification

Column 19, Line 11:
"422ii" should recite -- $422i_1$ --

Column 19, Line 13:
"424i2" should recite -- $424i_2$ --

Column 19, Line 15:
"426i3" should recite -- $426i_3$ --

Column 19, Line 17:
"4284" should recite -- $428i_4$ --

Signed and Sealed this  
Second Day of July, 2024

Katherine Kelly Vidal  
*Director of the United States Patent and Trademark Office*